United States Patent
Lee et al.

(10) Patent No.: US 11,040,057 B2
(45) Date of Patent: Jun. 22, 2021

(54) PHARMACEUTICAL COMPOSITIONS AND METHODS FOR POTENTIATING GENE SILENCING

(71) Applicant: OliX Pharmaceuticals, Inc., Gyeonggi-do (KR)

(72) Inventors: Dong Ki Lee, Gyeonggi-do (KR); Da Seul Son, Gyeonggi-do (KR); Yang Hee Kim, Gyeonggi-do (KR)

(73) Assignee: OliX Pharmaceuticals, Inc., Gyeonggi-do (KR)

( * ) Notice: Subject to any disclaimer, the term of this patent is extended or adjusted under 35 U.S.C. 154(b) by 41 days.

(21) Appl. No.: 16/313,754

(22) PCT Filed: Jun. 29, 2017

(86) PCT No.: PCT/KR2017/006923
§ 371 (c)(1),
(2) Date: Dec. 27, 2018

(87) PCT Pub. No.: WO2018/004284
PCT Pub. Date: Jan. 4, 2018

(65) Prior Publication Data
US 2019/0321388 A1    Oct. 24, 2019

(30) Foreign Application Priority Data
Jun. 29, 2016   (KR) .................. 10-2016-0081914

(51) Int. Cl.
| | | |
|---|---|---|
| *A61K 31/713* | (2006.01) | |
| *C12N 15/113* | (2010.01) | |
| *A61K 31/137* | (2006.01) | |
| *A61K 31/277* | (2006.01) | |
| *A61K 31/4422* | (2006.01) | |
| *A61K 31/4439* | (2006.01) | |
| *A61K 31/444* | (2006.01) | |
| *A61K 31/497* | (2006.01) | |
| *A61K 31/554* | (2006.01) | |
| *A61K 31/665* | (2006.01) | |

(52) U.S. Cl.
CPC .......... *A61K 31/713* (2013.01); *A61K 31/137* (2013.01); *A61K 31/277* (2013.01); *A61K 31/444* (2013.01); *A61K 31/4422* (2013.01); *A61K 31/4439* (2013.01); *A61K 31/497* (2013.01); *A61K 31/554* (2013.01); *A61K 31/665* (2013.01); *C12N 15/113* (2013.01); *C12N 2310/11* (2013.01); *C12N 2310/14* (2013.01); *C12N 2310/315* (2013.01); *C12N 2310/321* (2013.01); *C12N 2310/346* (2013.01); *C12N 2310/3515* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,837,258 A | 11/1998 | Grotendorst |
| 7,078,196 B2 | 7/2006 | Tuschl et al. |
| 7,691,997 B2 | 4/2010 | Khvorova et al. |
| 7,700,541 B2 | 4/2010 | Tanaka et al. |
| 8,410,260 B2 | 4/2013 | Collin-Djangone et al. |
| 8,614,309 B2 | 12/2013 | Feinstein et al. |
| 8,802,733 B2 | 8/2014 | Ganesan et al. |
| 8,822,428 B2 | 9/2014 | Collin-Djangone et al. |
| 8,980,273 B1 | 3/2015 | Clube |
| 9,453,226 B2 | 9/2016 | Ambati et al. |
| 9,637,742 B2 | 5/2017 | Lee |
| 9,707,235 B1 | 7/2017 | Ambati |
| 10,059,949 B2 | 8/2018 | Lee et al. |
| 10,064,801 B2 | 9/2018 | Hong et al. |
| 10,125,362 B2 | 11/2018 | Hong |
| 10,214,744 B2 | 2/2019 | Lee |
| 10,238,749 B2 * | 3/2019 | Foster ................ A61P 13/12 |
| 10,358,648 B2 | 7/2019 | Lee et al. |
| 10,485,885 B2 * | 11/2019 | Besin ............... C08G 65/33317 |
| 2004/0138163 A1 | 7/2004 | McSwiggen et al. |
| 2004/0180351 A1 | 9/2004 | Giese et al. |
| 2004/0266707 A1 | 12/2004 | Leake et al. |
| 2005/0119202 A1 | 6/2005 | Kreutzer et al. |
| 2005/0171040 A1 * | 8/2005 | Polisky .......... C12Y 207/11001 514/44 A |
| 2005/0282188 A1 | 12/2005 | Haeberli et al. |
| 2006/0069050 A1 | 3/2006 | Rana |

(Continued)

FOREIGN PATENT DOCUMENTS

| | | |
|---|---|---|
| CN | 102719432 | 10/2012 |
| EP | 2631291 | 8/2013 |

(Continued)

OTHER PUBLICATIONS

Ambati et al., "Mechanisms of Age-Related Macular Degeneration," Neuron, 75: 26-39 (2012).
Bolcato-Bellemin et al., "Sticky overhangs enhance siRNA-mediated gene silencing," PNAS, vol. 104, No. 41, pp. 16050-16055 (2007).

(Continued)

*Primary Examiner* — Sean McGarry
(74) *Attorney, Agent, or Firm* — Morgan, Lewis & Bockius LLP

(57) ABSTRACT

In various aspects and embodiments, the invention provides compounds or agents that potentiate siRNA cellular entry or activity, and provides methods for identifying such compounds or agents. Exemplary agents that act as L-type calcium channel blockers are described herein, and are shown to potentiate gene silencing with cp-asiRNAs.

18 Claims, 6 Drawing Sheets

Specification includes a Sequence Listing.

(56) References Cited

U.S. PATENT DOCUMENTS

| | | | |
|---|---|---|---|
| 2006/0094032 A1 | 5/2006 | Fougerolles et al. | |
| 2006/0105976 A1 | 5/2006 | Soutschek et al. | |
| 2006/0134787 A1 | 6/2006 | Zamore et al. | |
| 2006/0142228 A1 | 6/2006 | Ford et al. | |
| 2006/0160123 A1 | 7/2006 | Quay | |
| 2007/0161596 A1* | 7/2007 | McSwiggen | C12N 15/1137 514/44 A |
| 2007/0218495 A1 | 9/2007 | Birmingham et al. | |
| 2007/0275914 A1 | 11/2007 | Manoharan et al. | |
| 2008/0125386 A1 | 5/2008 | Rana et al. | |
| 2008/0188430 A1 | 8/2008 | Usman et al. | |
| 2009/0004668 A1 | 1/2009 | Chen et al. | |
| 2009/0012022 A1 | 1/2009 | Milner et al. | |
| 2009/0130751 A1 | 5/2009 | Davidson et al. | |
| 2009/0191625 A1 | 7/2009 | Khvorova et al. | |
| 2009/0208564 A1 | 8/2009 | Li et al. | |
| 2010/0197023 A1 | 8/2010 | Leake et al. | |
| 2010/0254945 A1 | 10/2010 | Ge et al. | |
| 2010/0291681 A1 | 11/2010 | Khvorova et al. | |
| 2011/0028534 A1 | 2/2011 | Shepard et al. | |
| 2011/0054160 A1 | 3/2011 | Manoharan | |
| 2011/0237647 A1 | 9/2011 | Shirasawa et al. | |
| 2011/0237648 A1 | 9/2011 | Khvorova et al. | |
| 2011/0251258 A1 | 10/2011 | Samarsky et al. | |
| 2011/0263680 A1 | 10/2011 | Khvorova et al. | |
| 2011/0269816 A1 | 11/2011 | Kaspar et al. | |
| 2012/0016011 A1 | 1/2012 | Pickering et al. | |
| 2012/0238017 A1 | 9/2012 | Lee et al. | |
| 2013/0011922 A1 | 1/2013 | Quay et al. | |
| 2013/0035368 A1 | 2/2013 | Avkin-Nachum et al. | |
| 2013/0115613 A1 | 5/2013 | Madiraju et al. | |
| 2013/0123342 A1 | 5/2013 | Brown | |
| 2013/0131142 A1 | 5/2013 | Libertine et al. | |
| 2013/0190387 A1 | 7/2013 | Feinstein | |
| 2013/0273657 A1 | 10/2013 | Lee | |
| 2013/0317080 A1 | 11/2013 | Rajeev et al. | |
| 2014/0094501 A1 | 4/2014 | Puri et al. | |
| 2014/0227266 A1 | 8/2014 | Lee et al. | |
| 2014/0249304 A1 | 9/2014 | Lee et al. | |
| 2014/0328903 A1 | 11/2014 | Santel et al. | |
| 2014/0350068 A1 | 11/2014 | Feinstein et al. | |
| 2015/0111948 A1 | 4/2015 | Hong | |
| 2015/0184163 A1 | 7/2015 | Wilson et al. | |
| 2016/0017056 A1 | 1/2016 | Clube | |
| 2016/0122764 A1 | 5/2016 | Chae et al. | |
| 2016/0235856 A1* | 8/2016 | Montefeltro | C07D 217/04 |
| 2016/0319278 A1 | 11/2016 | Khvorova et al. | |
| 2016/0340674 A1* | 11/2016 | Jin | A61K 31/444 |
| 2017/0189541 A1* | 7/2017 | Foster | A61P 27/02 |
| 2017/0298358 A1 | 10/2017 | Lee et al. | |
| 2017/0369882 A1 | 12/2017 | Khvorova et al. | |
| 2019/0117659 A1* | 4/2019 | Friedman | A61K 45/06 |
| 2019/0185852 A1* | 6/2019 | Hussain | C12N 15/113 |
| 2019/0298842 A1* | 10/2019 | Foster | A61P 5/38 |

FOREIGN PATENT DOCUMENTS

| | | |
|---|---|---|
| JP | 2012502991 | 2/2012 |
| KR | 101207561 | 12/2012 |
| KR | 10-1595152 B1 | 2/2016 |
| WO | WO0244321 | 6/2002 |
| WO | WO02055693 | 7/2002 |
| WO | WO2005062937 | 7/2005 |
| WO | WO 2005063213 A1 | 7/2005 |
| WO | WO2005079533 | 9/2005 |
| WO | WO 2006084005 A2 | 8/2006 |
| WO | WO2007002470 | 2/2007 |
| WO | WO2007128477 | 11/2007 |
| WO | WO2008109377 | 9/2008 |
| WO | WO2009020344 | 2/2009 |
| WO | WO2009029688 | 3/2009 |
| WO | WO2009029690 | 3/2009 |
| WO | WO2009078685 | 6/2009 |
| WO | WO2009105260 | 8/2009 |
| WO | WO2010033247 | 3/2010 |
| WO | WO2010090762 | 8/2010 |
| WO | WO201119887 | 9/2011 |
| WO | WO2012078536 | 6/2012 |
| WO | WO2012118911 | 9/2012 |
| WO | WO2014043291 | 3/2014 |
| WO | WO2015002513 | 1/2015 |
| WO | WO2015015498 | 2/2015 |
| WO | WO 2015171641 A1 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

Bramsen et al., "Improved silencing properties using small internally segmented interfering RNAs," Nucleic Acids Research, (2007), pp. 5886-5897, vol. 35.

Bushati et al., "MicroRNAs in Neurodegeneration," Current Opin Neurobiol, 18: 292-296 (2008).

Caplen et al., "Specific inhibition of gene expression by small double-stranded RNAs in invertebrate and vertebrate systems," Proc. Natl. Acad. Sci. USA, (2001), pp. 9742-9747, vol. 98, No. 17.

Chang et al., "Structural diversity repertoire of gene silencing small interfering RNAs," Nucleic acid therapeutics, (2011), 21(3), 125-131.

Chang et al., "The design, preparation, and evaluation of asymmetric small interfering RNA for specific gene silencing in mammalian cells," Methods Mol Biol. 2013; 942:135-52.

Chang et al., "Asymmetric shorter-duplex siRNA structures trigger efficient gene silencing with reduced nonsoecific effects," Mol Ther, (2009), 17(4):725-732.

Chiu et al., "siRNA Function in RNAi: A Chemical Modification Analysis," RNA, 9: 1034-1048 (2003).

Doench et al., "siRNAs Can Function as miRNAs," Gene Dev, 17(4): 438-442 (2003).

Doench et al., "Specificity of MicroRNA Target Selection in Translation Repression," Gene Dev, 18: 504-511 (2004).

Elbashir et al., "Duplexes of 21-nucleotide RNAs mediate RNA interference in cultured mammalian cells," Nature, (2001), 411:494-498.

Elbashir et al., "Functional anatomy of siRNAs for mediating efficient RNAi in *Drosophila melanogaster* embryo lysate," The EMBO Journal, (2001), pp. 6877-6888, vol. 20, No. 23.

Fire, "RNA-triggered gene silencing," Trends in Genetics, (1999), vol. 15, No. 9, pp. 358-363.

Fire et al., "Potent and specific genetic interference by double-stranded RNA in Caenorhabditis elegans," Nature, (1998), pp. 806-811, vol. 391.

Grimm, "Small silencing RNAs: State of the art," Advanced Drug Delivery Reviews, 61: 672-703 (2009).

Hammond et al., "Post-Transcriptional Gene Silencing by Double-Stranded RNA," Nature Reviews Genetics, (2001), vol. 2: 110-119.

Hong et al., "Effect of the guide strand 3'-end structure on the gene-silencing potency of asymmetric siRNA," Biochemical Journal, (2014), 461(3): 427-434.

Huang et al., "Targeting the ANGPT-TIE2 Pathway in Malignancy," Nat Rev Cancer, 10: 575-585 (2010).

Hwang, "Development of Cell-Penetrating Asymmetric Interfering RNA Targeting Connective Tissue Growth Factor," Journal of Investigative Dermatology, (2016), 136(11), 2305-2313.

Jackson et al., "Expression Profiling Reveals Off-Target Gene Regulation by RNAi," Nat Biotechnol, 21: 635-637 (2003).

Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).

Jo et al., "Selection and optimization of asymmetric siRNA targeting the human c-MET gene," Mol Cell, 32:(6) 543-548 (2011).

(56) References Cited

OTHER PUBLICATIONS

Joshi, et al., "siRNA: novel therapeutics from functional genomics," Biotechnology and Genetic Enginnering Reviews (2014) vol. 30, No. 1, pp. 1-30.
Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).
Kim et al., "Synthetic dsRNA Dicer substrates enhance RNAi potency and efficacy," Nature Biotechnology, 23: 222-226 (2005).
Kore et al., "Chemical modification of synthetic RNAi agents and in vivo delivery techniques," Curr Bioactive Compounds, 4:6-14 (2008).
Kubo et al., "Modified 27nt dsRNAs with Dramatically Enhanced Stability in Serum and Long-Term RNAi Activity," Oligonucleotides, 17:445-464 (2007).
Kulkarni et al., "Evidence of Off-Target Effects Associated with Long dsRNAs in *Drosophila melanogaster* Cell-Based Assays," Nat Methods, 3: 833-838 (2006).
Lee et al., "Asymmetric RNA Duplexes as Next Generation RNAi Inducers," Gene Silencing: Theory, Techniques and Applications, (2010), pp. 343-348.
Li et al., "Inhibition of connective tissue growth factor by siRNA prevents liver fibrosis in rats," The Journal of Gene Medicine, (2006), 8:889-900.
Lima et al., "Human Dicer Binds Short Single-strand and Double-strand RNA with High Affinity and Interacts with Different Regions of the Nucleic Acids," The Journal of Biological Chemistry (2009), 284:2535-2548.
Luo et al., "Inhibition of Connective Tissue Growth Factor by Small Interfering RNA Prevents Renal Fibrosis in Rats Undergoing Chronic Allograft Nephropathy," Transplantation Proceedings, (2008), 40:2365-2369.
Marques et al., "A structural basis for discriminating between self and nonself double-stranded RNAs in mammalian cells," Nature Biotechnology, 24: 559-565 (2006).
Martinez et al., "Singe-Stranded Antisense siRNAs Guide Target RNA Cleavage in RNAi," Cell, 110: 563-574 (2002).
Opalinska et al., "Nucleic-acid Therapeutics: Basic Principles and Recent Applications," Nature Rev, 1 (7): 503-514 (2002).
Paroo et al., "Challenges for RNAi in vivo," Trends in Biotech, 22(8): 390-394 (2004).
Patel et al., "A Novel Protective Role for the Innate Immunity Toll-Like Receptor 3 (TLR3) in the Retina via Stat3," Mol Cell Neurosci, 63: 38-48 (2014).
Raouane et al., "Lipid conjugated oligonucleotides: a useful strategy for delivery," Bioconjugate Chem, 23:1091-104 (2012).
Rose et al., "Functional Polarity is Introduced by Dicer Processing of Short Substrate RNAs," Nucleic Acids Res, 33: 4140-4156 (2005).
Sano et al., "Effect of asymmetric terminal structures of short RNA duplexes on the RNA interference activity and strand selection," Nucleic Acids Research (2008), 36: 5812-5821.
Sharp et al., "RNA-interference-2001," Genes & Development, (2001), 15:485-490.
Sioud et al., "Cationic liposome-mediated delivery of siRNAs in adult mice," Biochem Biophys Res Commun. Dec. 26, 2003; 312(4):1220-5.
Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (2008).
Song et al., "The Crystal Structure of the Argonaute2 PAZ Domain Reveals an RNA Binding Motif in RNAi Effector Complexes," Nat Struct Biol, 10(12): 1026-1032 (2003).
Soutschek et al., "Therapeutic Silencing of an Endogenous Gene by Systemic Adminstration of Modified siRNAs," Nature, 432: 173-178 (2004).
Sun et al., "Asymmetric RNA duplexes mediate RNA interference in mammalian cells," Nature Biotechnology, 26: 1379-1382 (2008).
Ui-Tei et al., "Essential Notes Regarding the Design of Functional siRNAs for Efficient Mammalian RNAi," J Biomed Biotechnol, 2006; 2006(4):65052. doi: 10.1155/JBB/2006/65052.
Ui-Tei et al., "Guidelines for the selection of highly effective siRNA sequences for mammalian and chick RNA interference," (2004), Nucleic Acids Research, vol. 32, pp. 936-948.
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (2009).
Yang et al., "HEN1 recognizes 21-24 nt small RNA duplexes and deposits a methyl group onto the 2' OH of the 3' terminal nucleotide," Nucleic Acids Research, 34: 667-675 (2006).
Yuan et al., "Asymmetric siRNA: New Strategy to Improve Specificity and Reduce Off-Target Gene Expression", Human Gene Therapy 23:521-532 (2013).
Zamore, "RNA interference: listening to the sound of silence," Nature Structural Biology, (2001), 8(9):746-750.
Juliano, "The delivery of therapeutic oligonucleotides," Nucleic Acids Research, vol. 14, No. 14, pp. 6518-6548, Apr. 15, 2016.
International Search Report & Written Opinion, PCT Appl. No. PCT/KR2017/006923, dated Oct. 11, 2017, 12 pages.

\* cited by examiner

SEQUENCE LISTING

<160> NUMBER OF SEQ ID NOS: 150

<210> SEQ ID NO 1
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 1
gcgaggagug ggugugugat t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 2
uccucgcagc auuucccggt t                                            21

<210> SEQ ID NO 3
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 3
aggagugggu guguga                                                  16

<210> SEQ ID NO 4
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

```
<400> SEQUENCE: 4
uccucgcagc auuucccggt t                                              21

<210> SEQ ID NO 5
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 5
aggagugggu guguga                                                    16

<210> SEQ ID NO 6
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 6
ucacacaccc acuccucgca gcauucccg g                                    31

<210> SEQ ID NO 7
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 7
agaccugugg gaugggcaut t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 8
caggucuugg aacaggcgct t                                              21

<210> SEQ ID NO 9
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 9
ccugugggau gggcau                                                    16

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: (1)..(19)
<223> OTHER INFORMATION: RNA

<400> SEQUENCE: 10
caggucuugg aacaggcgct t                                              21

<210> SEQ ID NO 11
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 11
ccugugggau gggcau                                                    16

<210> SEQ ID NO 12
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 12
augcccaucc cacaggucuu ggaacaggcg c                                   31

<210> SEQ ID NO 13
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 13
acaggaagau guacggagat t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 14
uuccuguagu acagcgauut t                                              21

<210> SEQ ID NO 15
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 15
ggaagaugua cggaga                                                    16

<210> SEQ ID NO 16
```

```
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 16
uuccuguagu acagcgauut t                                              21

<210> SEQ ID NO 17
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 17
ggaagaugua cggaga                                                    16

<210> SEQ ID NO 18
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 18
ucuccguaca ucuuccugua guacagcgau u                                   31

<210> SEQ ID NO 19
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 19
gcaccagcau gaagacauat t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 20
uaugucuuca ugcuggugct t                                              21

<210> SEQ ID NO 21
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 21
```
ccagcaugaa gacaua                                                    16

<210> SEQ ID NO 22
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 22
uaugucuuca ugcuggugct t                                              21

<210> SEQ ID NO 23
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 23
ccagcaugaa gacaua                                                    16

<210> SEQ ID NO 24
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 24
uaugucuuca ugcuggucca gccagaaagc u                                   31

<210> SEQ ID NO 25
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 25
gaagacauac cgagcuaaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 26
uuuagcucgg uaugucuuct t                                              21

<210> SEQ ID NO 27
<211> LENGTH: 16
<212> TYPE: RNA

<213> ORGANISM: Artificial Sequence
<220> FEATURE:
<223> OTHER INFORMATION: Synthetic Sequence

<400> SEQUENCE: 27
gacauaccga gcuaaa    16

<210> SEQ ID NO 28
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 28
uuuagcucgg uaugucuuct t    21

<210> SEQ ID NO 29
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 29
gacauaccga gcuaaa    16

<210> SEQ ID NO 30
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 30
uuuagcucgg uaugucuuca ugcuggugca g    31

<210> SEQ ID NO 31
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 31
gcuaaauucu guggaguaut t    21

<210> SEQ ID NO 32
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 32
auacuccaca gaauuuagct t    21

<210> SEQ ID NO 33
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 33
aaauucugug gaguau                                                      16

<210> SEQ ID NO 34
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 34
auacuccaca gaauuuagct t                                                21

<210> SEQ ID NO 35
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 35
aaauucugug gaguau                                                      16

<210> SEQ ID NO 36
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 36
auacuccaca gaauuuagcu cgguaugucu u                                     31

<210> SEQ ID NO 37
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 37
gcgaggucau gaagaagaat t                                                21

<210> SEQ ID NO 38
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)

<223> OTHER INFORMATION: RNA

<400> SEQUENCE: 38
uuguucuuca ugaccucgct t                                          21

<210> SEQ ID NO 39
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 39
aggucaugaa gaagaa                                                16

<210> SEQ ID NO 40
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 40
uuguucuuca ugaccucgct t                                          21

<210> SEQ ID NO 41
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 41
aggucaugaa gaagaa                                                16

<210> SEQ ID NO 42
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 42
uuguucuuca ugaccucgcc gucagggcac u                               31

<210> SEQ ID NO 43
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 43
uggaagagaa cauuaagaat t                                          21

<210> SEQ ID NO 44
<211> LENGTH: 21
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 44
uucuuaaugu ucucuuccat t                                              21

<210> SEQ ID NO 45
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 45
aagagaacau uaagaa                                                    16

<210> SEQ ID NO 46
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 46
uucuuaaugu ucucuuccat t                                              21

<210> SEQ ID NO 47
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 47
aagagaacau uaagaa                                                    16

<210> SEQ ID NO 48
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 48
uucuuaaugu ucucuuccag gucagcuucg c                                   31

<210> SEQ ID NO 49
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 49
cggcuuaccg acuggaagat t                                              21
```

<210> SEQ ID NO 50
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 50
ucuuccaguc gguaagccgt t                                              21

<210> SEQ ID NO 51
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 51
cuuaccgacu ggaaga                                                    16

<210> SEQ ID NO 52
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 52
ucuuccaguc gguaagccgt t                                              21

<210> SEQ ID NO 53
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 53
cuuaccgacu ggaaga                                                    16

<210> SEQ ID NO 54
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 54
ucuuccaguc gguaagccgc gagggcaggc c                                   31

<210> SEQ ID NO 55
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

```
<400> SEQUENCE: 55
gcaugaagcc agagagugat t                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 56
ucacucucug gcuucaugct t                                              21

<210> SEQ ID NO 57
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 57
ugaagccaga gaguga                                                    16

<210> SEQ ID NO 58
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 58
ucacucucug gcuucaugct t                                              21

<210> SEQ ID NO 59
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 59
ugaagccaga gaguga                                                    16

<210> SEQ ID NO 60
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 60
ucacucucug gcuucaugcc caugucuccg u                                   31

<210> SEQ ID NO 61
<211> LENGTH: 21
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 61
caccauaggu agaauguaat t                                              21

<210> SEQ ID NO 62
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 62
uuacauucua ccuauggugt t                                              21

<210> SEQ ID NO 63
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 63
cauagguaga auguaa                                                    16

<210> SEQ ID NO 64
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 64
uuacauucua ccuauggugt t                                              21

<210> SEQ ID NO 65
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 65
cauagguaga auguaa                                                    16

<210> SEQ ID NO 66
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 66
uuacauucua ccuauggugu ucagaaauug a                                   31
```

```
<210> SEQ ID NO 67
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 67
ccugcaggcu agagaagcat t                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 68
ugcuucucua gccugcaggt t                                              21

<210> SEQ ID NO 69
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 69
gcaggcuaga gaagca                                                    16

<210> SEQ ID NO 70
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 70
ugcuucucua gccugcaggt t                                              21

<210> SEQ ID NO 71
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 71
gcaggcuaga gaagca                                                    16

<210> SEQ ID NO 72
<211> LENGTH: 31
<212> TYPE: RNA
<213> ORGANISM: Artificial Sequence
<220> FEATURE:
<223> OTHER INFORMATION: Synthetic Sequence
```

```
<400> SEQUENCE: 72
ugcuucucua gccugcagga ggcguuguca u                               31

<210> SEQ ID NO 73
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 73
ccagagagug agagacauut t                                          21

<210> SEQ ID NO 74
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 74
aaugucucuc acucucuggt t                                          21

<210> SEQ ID NO 75
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 75
gagagugaga gacauu                                                16

<210> SEQ ID NO 76
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 76
aaugucucuc acucucuggt t                                          21

<210> SEQ ID NO 77
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 77
gagagugaga gacauu                                                16

<210> SEQ ID NO 78
<211> LENGTH: 31
```

```
<212> TYPE: RNA
<213> ORGANISM: Artificial Sequence
<220> FEATURE:
<223> OTHER INFORMATION: Synthetic Sequence

<400> SEQUENCE: 78
aaugucucuc acucucuggc uucaugccau g                                      31

<210> SEQ ID NO 79
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 79
gcgaagcuga ccuggaagat t                                                 21

<210> SEQ ID NO 80
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 80
ucuuccaggu cagcuucgct t                                                 21

<210> SEQ ID NO 81
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 81
aagcugaccu ggaaga                                                       16

<210> SEQ ID NO 82
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 82
ucuuccaggu cagcuucgct t                                                 21

<210> SEQ ID NO 83
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 83
```
aagcugaccu ggaaga                                                    16

<210> SEQ ID NO 84
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 84
ucuuccaggu cagcuucgca aggccugacc a                                   31

<210> SEQ ID NO 85
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 85
ccggagacaa ugacaucuut t                                              21

<210> SEQ ID NO 86
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 86
aagaugucau ugucuccggt t                                              21

<210> SEQ ID NO 87
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 87
gagacaauga caucuu                                                    16

<210> SEQ ID NO 88
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 88
aagaugucau ugucuccggt t                                              21

<210> SEQ ID NO 89
<211> LENGTH: 16
<212> TYPE: RNA
<213> ORGANISM: Artificial Sequence

```
<220> FEATURE:
<223> OTHER INFORMATION: Synthetic Sequence

<400> SEQUENCE: 89
gagacaauga caucuu                                                      16

<210> SEQ ID NO 90
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 90
aagaugucau ugucuccggg acaguuguaa u                                     31

<210> SEQ ID NO 91
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 91
ucuuugaauc gcuguacuat t                                                21

<210> SEQ ID NO 92
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 92
uaguacagcg auucaaagat t                                                21

<210> SEQ ID NO 93
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 93
uugaaucgcu guacua                                                      16

<210> SEQ ID NO 94
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 94
uaguacagcg auucaaagat t                                                21
```

<210> SEQ ID NO 95
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 95
uugaaucgcu guacua                                                         16

<210> SEQ ID NO 96
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 96
uaguacagcg auucaaagau gucauugucu c                                        31

<210> SEQ ID NO 97
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 97
uugcgaagcu gaccuggaat t                                                   21

<210> SEQ ID NO 98
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 98
uuccagguca gcuucgcaat t                                                   21

<210> SEQ ID NO 99
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 99
cgaagcugac cuggaa                                                         16

<210> SEQ ID NO 100
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 100
uuccagguca gcuucgcaat t                                              21

<210> SEQ ID NO 101
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 101
cgaagcugac cuggaa                                                    16

<210> SEQ ID NO 102
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 102
uuccagguca gcuucgcaag gccugaccau g                                   31

<210> SEQ ID NO 103
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 103
caacuaugau uagagccaat t                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 104
uuggcucuaa ucauaguugt t                                              21

<210> SEQ ID NO 105
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 105
cuaugauuag agccaa                                                    16

<210> SEQ ID NO 106
<211> LENGTH: 21
<212> TYPE: DNA
<213> ORGANISM: Artificial Sequence
<220> FEATURE:

```
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 106
uuggcucuaa ucauaguugt t                                              21

<210> SEQ ID NO 107
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 107
cuaugauuag agccaa                                                    16

<210> SEQ ID NO 108
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 108
uuggcucuaa ucauaguugg gucugggcca a                                   31

<210> SEQ ID NO 109
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 109
guaccagugc acgugccugt t                                              21

<210> SEQ ID NO 110
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 110
caggcacgug cacugguact t                                              21

<210> SEQ ID NO 111
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 111
ccagugcacg ugccug                                                    16
```

```
<210> SEQ ID NO 112
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 112
caggcacgug cacugguact t                                              21

<210> SEQ ID NO 113
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 113
ccagugcacg ugccug                                                    16

<210> SEQ ID NO 114
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 114
caggcacgug cacugguacu ugcagcugcu c                                   31

<210> SEQ ID NO 115
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 115
agugcauccg uacucccaat t                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 116
uugggaguac ggaugcacut t                                              21

<210> SEQ ID NO 117
<211> LENGTH: 16
<212> TYPE: RNA
<213> ORGANISM: Artificial Sequence
<220> FEATURE:
<223> OTHER INFORMATION: Synthetic Sequence
```

```
<400> SEQUENCE: 117
gcauccguac ucccaa                                                 16

<210> SEQ ID NO 118
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 118
uugggaguac ggaugcacut t                                           21

<210> SEQ ID NO 119
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 119
gcauccguac ucccaa                                                 16

<210> SEQ ID NO 120
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 120
uugggaguac ggaugcacuu uuugcccuuc u                                31

<210> SEQ ID NO 121
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 121
caugauguuc aucaagacct t                                           21

<210> SEQ ID NO 122
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 122
ggucuugaug aacaucaugt t                                           21

<210> SEQ ID NO 123
<211> LENGTH: 16
```

```
<212> TYPE: RNA
<213> ORGANISM: Artificial Sequence
<220> FEATURE:
<223> OTHER INFORMATION: Synthetic Sequence

<400> SEQUENCE: 123
gauguucauc aagacc                                                          16

<210> SEQ ID NO 124
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 124
ggucuugaug aacaucaugt t                                                    21

<210> SEQ ID NO 125
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 125
gauguucauc aagacc                                                          16

<210> SEQ ID NO 126
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 126
ggucuugaug aacaucaugu ucuucuucau g                                         31

<210> SEQ ID NO 127
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 127
ccaugaccgc cgccaguaut t                                                    21

<210> SEQ ID NO 128
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 128
```
auacuggcgg cggucauggt t          21

<210> SEQ ID NO 129
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 129
ugaccgccgc caguau          16

<210> SEQ ID NO 130
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 130
auacuggcgg cggucauggt t          21

<210> SEQ ID NO 131
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 131
ugaccgccgc caguau          16

<210> SEQ ID NO 132
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 132
auacuggcgg cggucauggu uggcacugcg g          31

<210> SEQ ID NO 133
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 133
gaacauuaag aagggcaaat t          21

<210> SEQ ID NO 134
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature -continued

```
<222> LOCATION: (1)..(19)
<223> OTHER INFORMATION: RNA

<400> SEQUENCE: 134
uuugcccuuc uuaauguuct t                                              21

<210> SEQ ID NO 135
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 135
cauuaagaag ggcaaa                                                    16

<210> SEQ ID NO 136
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 136
uuugcccuuc uuaauguuct t                                              21

<210> SEQ ID NO 137
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 137
cauuaagaag ggcaaa                                                    16

<210> SEQ ID NO 138
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 138
uuugcccuuc uuaauguucu cuuccagguc a                                   31

<210> SEQ ID NO 139
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 139
ggaagacacg uuuggcccat t                                              21

<210> SEQ ID NO 140
<211> LENGTH: 21
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 140
ugggccaaac gugucuucct t                                              21

<210> SEQ ID NO 141
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 141
agacacguuu ggccca                                                    16

<210> SEQ ID NO 142
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: RNA

<400> SEQUENCE: 142
ugggccaaac gugucuucct t                                              21

<210> SEQ ID NO 143
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 143
agacacguuu ggccca                                                    16

<210> SEQ ID NO 144
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 144
ugggccaaac gugucuucca gucgguaagc c                                   31

<210> SEQ ID NO 145
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: OMe modification
<222> LOCATION: (1)..(1)
<220> FEATURE:
<221> NAME/KEY: OMe modification
<222> LOCATION: (3)..(3)
<220> FEATURE:
<221> NAME/KEY: OMe modification
```

```
<222> LOCATION: (5)..(5)
<220> FEATURE:
<221> NAME/KEY: OMe modification
<222> LOCATION: (7)..(7)
<220> FEATURE:
<221> NAME/KEY: OMe modification
<222> LOCATION: (9)..(9)
<220> FEATURE:
<221> NAME/KEY: OMe modification
<222> LOCATION: (11)..(11)
<220> FEATURE:
<221> NAME/KEY: OMe modification
<222> LOCATION: (13)..(13)
<220> FEATURE:
<221> NAME/KEY: Phosphorothioate (PS) modification
<222> LOCATION: (14)..(16)
<220> FEATURE:
<221> NAME/KEY: OMe modification
<222> LOCATION: (15)..(15)
<220> FEATURE:
<221> NAME/KEY: misc_binding
<222> LOCATION: (16)..(16)
<223> OTHER INFORMATION: Cholesterol

<400> SEQUENCE: 145
cuuaccgacu ggaaga                                               16

<210> SEQ ID NO 146
<211> LENGTH: 31
<212> TYPE: RNA
<213> ORGANISM: Artificial Sequence
<220> FEATURE:
<223> OTHER INFORMATION: Synthetic Sequence
<220> FEATURE:
<221> NAME/KEY: OMe modification
<222> LOCATION: (13)..(31)
<220> FEATURE:
<221> NAME/KEY: Phosphorothioate (PS) modification
<222> LOCATION: (28)..(31)

<400> SEQUENCE: 146
ucuuccaguc gguaagccgc gagggcaggc c                              31

<210> SEQ ID NO 147
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 147
caagggcctc ttctgtgact                                           20

<210> SEQ ID NO 148
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 148
ccgtcggtac atactccaca                                           20

<210> SEQ ID NO 149
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 149
```

```
gagtcaacgg atttggtcgt                                              20

<210> SEQ ID NO 150
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 150
gacaagcttc ccgttctcag                                              20
```

PHARMACEUTICAL COMPOSITIONS AND METHODS FOR POTENTIATING GENE SILENCING

PRIORITY

The present application claims priority to Korean Patent Application No. KR 10-2016-0081914, filed Jun. 29, 2016, the contents of which are herein incorporated by reference in their entireties.

FIELD

The present invention provides compounds or agents that potentiate siRNA cellular entry or activity. The invention further provides methods for identifying such compounds or agents.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: OLX-004PC-Sequence Listing; date recorded: Jun. 27, 2017; file size: 33 KB).

BACKGROUND

RNA interference (RNAi) provides the ability to inhibit gene expression in a highly specific and efficient manner. RNAi leads to degradation of target mRNA by introducing into cells a double-stranded RNA, which comprises a sense strand having a sequence homologous to the mRNA of the target gene and an antisense strand having a sequence complementary to the mRNA of the target gene.

For the development of effective therapeutic agents based on siRNA, technical hurdles associated with, for example, stability, cell entry, and silencing efficiency, must be overcome. For example, effective in vivo delivery is challenging because siRNA cannot pass through the cell membrane, due to the negative charge of the phosphate backbone structure. While in the case of in vitro delivery there are many reagents employing cationic lipids and cationic polymers to enhance cell penetration, these reagents are not suitable for use in a therapeutic context.

Pharmaceutical compositions and methods for improving or potentiating siRNA activity, including compositions that enhance siRNA cell entry, are needed to advance this promising technology.

SUMMARY OF THE INVENTION

In various aspects and embodiments, the invention provides compounds or agents that potentiate siRNA cellular entry or activity. The present invention further provides methods for identifying such agents. Exemplary agents that act as L-type calcium channel blockers are described herein, and which are demonstrated to potentiate cellular entry of siRNAs.

In one aspect, the disclosure provides pharmaceutical compositions comprising an siRNA, such as a cell-penetrating asymmetric small interfering RNA (cp-asiRNA); and an L-type calcium channel blocker. The L-type calcium channel blocker enhances cellular penetration of the siRNA, leading to more efficient gene silencing. In some embodiments, the L-type calcium channel blocker is dihydropyridine or non-dihydropyridine L-type calcium channel blocker. The pharmaceutical compositions can be formulated for various delivery routes, including topical, pulmonary, and parenteral, for use in methods of treatment.

In other aspects, the invention provides a method of gene silencing in a subject, where the method comprises administering to the subject an effective amount of a small interfering RNA (siRNA); and an L-type calcium channel blocker. The siRNA and the L-type calcium channel blocker can be administered as a single pharmaceutical composition, or in some embodiments the siRNA and the L-type calcium channel blocker are administered as separate pharmaceutical compositions. In some embodiments, the siRNA is an asymmetric siRNA (asiRNA), such as a cell penetrating asiRNA (cp-asiRNA) or a long-antisense asiRNA (lasiRNA). The L-type calcium channel blocker may be a dihydropyridine L-type calcium channel blocker, or a non-dihydropyridine L-type calcium channel blocker. In various embodiments, one or both of the siRNA and L-type calcium channel blocker are formulated for topical, pulmonary, or parenteral delivery.

In another aspect, the disclosure provides a method of screening for a compound to improve the cellular entry or gene silencing activity of an siRNA, such as a cell-penetrating asymmetric small interfering RNA (cp-asiRNA) or a long-antisense asiRNA (lasiRNA). The method may comprise contacting the siRNA with a cell; and contacting a candidate compound with the cell; and detecting or quantifying siRNA in the cell, or in some embodiments, quantifying reduction in expression of a target RNA. By comparing siRNA penetration or activity with a control, compounds or agents that enhance or potentiate siRNA activity or cellular entry can be identified, optionally derivatized, and formulated as pharmaceutical compositions. In some embodiments, compounds can be screened for potentiating activity in high-throughput.

In additional embodiments, the method further comprises selecting a candidate compound that increases cellular penetration or activity of an siRNA (e.g., an asiRNA, e.g. a cp-asiRNA or a lasiRNA). These compounds can be formulated together with the siRNA, or formulated separately, and delivered to patients to potentiate the gene-silencing activity of the siRNA.

DETAILED DESCRIPTION OF THE INVENTION

Figure 1:
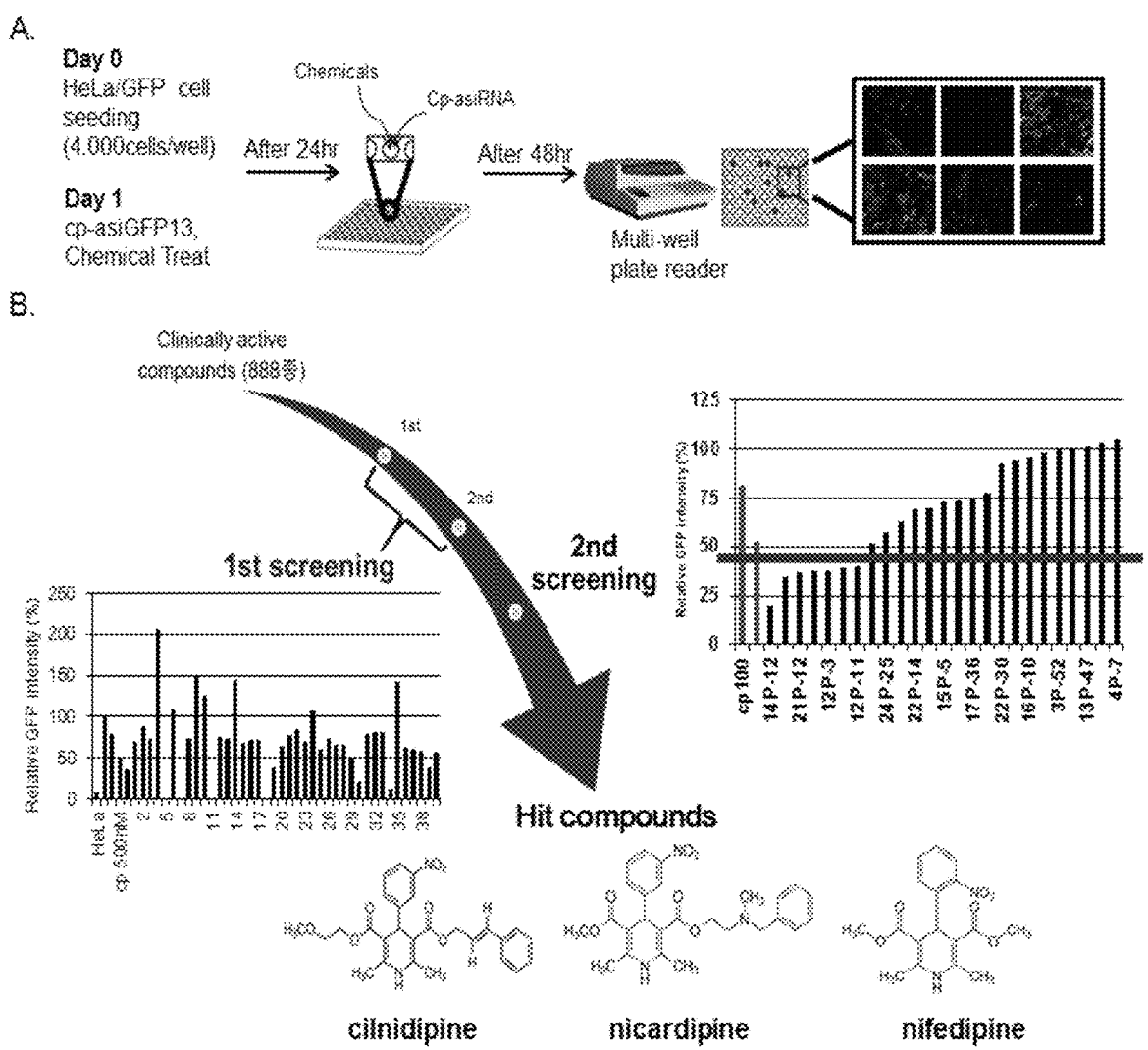
FIG. 1 depicts an exemplary scheme of high-throughput screening. Panel (A): Summary of high-throughput screening strategy. Panel (B): The result of high-throughput screening and hit compounds.

Unless defined otherwise, all technical and scientific terms used herein have the same meaning as is commonly understood by one of skill in the art to which this invention belongs. All patents and publications referred to herein are incorporated by reference in their entireties.

The present disclosure provides compositions and methods for potentiating gene silencing with siRNAs, as well as methods for preparing such compositions through compound screens. As disclosed herein, L-type calcium channel blockers potentiate the uptake of siRNAs, including cp-asiRNAs or lasiRNAs.

In one aspect, the disclosure provides pharmaceutical compositions comprising an siRNA, such as a cell-penetrating asymmetric small interfering RNA (cp-asiRNA) or a long-antisense asiRNA (lasiRNA); and an L-type calcium channel blocker.

As used herein, the term "RNAi" (RNA interference) refers to a mechanism by which a double-stranded RNA (dsRNA) comprising a first strand having a sequence complementary to the mRNA of a target gene, and a second strand having a sequence complementary to the first strand, is introduced into cells to induce the degradation of the target mRNA. The first strand may be an antisense strand, which refers to a polynucleotide which is substantially, that is about 80%, about 85%, about 90%, about 95%, about 96%, about 97%, about 98%, about 99%, or 100% complementary to a target mRNA. For example, an antisense strand may be complementary, in whole or in part, to a molecule of mRNA (messenger RNA), an RNA sequence that is not mRNA (e.g., microRNA, piwiRNA, tRNA, rRNA and hnRNA) or a sequence of DNA that is either coding or non-coding. The terms "antisense strand" and "guide strand" are used interchangeably herein. In various embodiments, the first strand generally has a length of from about 16 to about 50 nucleotides, such as about 16, 17, 18, 19, 20, 21, 22, 23, 24, and 25 nucleotides. In the first strand, the region complementary to the target nucleic acid may have a length of about 16 to about 31 nucleotides, about 19 to about 25 nucleotides, or about 19 to about 21 nucleotides. In addition, the second strand may be a sense strand, which refers to a polynucleotide that has the same nucleotide sequence, in whole or in part, as the target nucleic acid. The second strand may have a length of about 13 to about 25 nucleotides, about 13 to about 21 nucleotides, or about 16 to about 21 nucleotides. In various embodiments, the second strand may have about 10, 11, 12, 13, 14, 15, 16, 17, 18, 19, 20, 21, 22, 23, 24 or 25 nucleotides.

Asymmetric siRNAs (asiRNAs) are described in US 2012/0238017, which is hereby incorporated by reference in its entirety. In some embodiments, asiRNAs include configurations of "17+2A", "16+3A" and "15+4A". A 17+2A siRNA structure refers to a double-stranded siRNA molecule comprising a 19 nucleotide antisense strand and a 17 nucleotide sense strand having a sequence complementary thereto, wherein the 5' end of the antisense strand is a blunt end and the 3'-end of the antisense strand has a 2 nucleotide overhang. Likewise, the term 16+3A siRNA structure is a double-stranded siRNA molecule comprising a 19 nucleotide antisense strand and a 16 nucleotide sense strand having a sequence complementary thereto, wherein the 5' end of the antisense strand is a blunt end and the 3' end of the antisense strand has a 3 nucleotide overhang. A 15+4A siRNA structure is a double-stranded siRNA molecule comprising a 19 nucleotide antisense strand and a 15 nucleotide strand having a sequence complementary thereto, wherein the 5' end of the antisense strand is a blunt end and the 3' end of the antisense strand has a 4 nucleotide overhang. asiRNAs provide advantages in gene silencing efficiency, with a reduction in off-target effects by the sense strand.

In some embodiments, one or both ends of the asiRNA comprise an overhang on a 3' end. In some embodiments, the overhang is a dinucleotide overhang (e.g., dTdT).

In various embodiments, the asiRNA is a cell penetrating asymmetric siRNA or cp-asiRNA. Cp-asiRNAs are described, for example, in U.S. Patent Application Publication No. 2015/0111948, which is hereby incorporated by reference in its entirety. In some embodiments, the cp-asiRNA may internalize and silence a target gene in a cell without any transfection reagents.

In various embodiments, the cp-asiRNA comprises an asiRNA, wherein the phosphate backbone of at least one nucleotide in the nucleic acid molecule is substituted with phosphorothioate or phosphorodithioate, and further comprises a lipophilic compound conjugated thereto to facilitate cellular entry. In various embodiments, the phosphate backbone(s) of nucleotides in a region of the nucleic acid molecule, other than a region complementary to a target nucleic acid, may be substituted with phosphorothioate or phosphorodithioate. In some embodiments, the phosphate backbone of at least one nucleotide in the nucleic acid molecule may be substituted with phosphorothioate. In some embodiments, the lipophilic compound is selected from a lipid, a lipophilic peptide, and a lipophilic protein. The lipid may be at least one selected from cholesterol, tocopherol, and a long-chain fatty acid having 10 or more carbon atoms. In some embodiments, the lipophilic compound is cholesterol, cholestene, cholestane, cholestadiene, bile acid, cholic acid, deoxycholic acid, or dehydrocholic acid. In an embodiment, the lipophilic compound is cholesterol. The lipophilic compound may be conjugated to the end of the first or second strand of the nucleic acid molecule.

In various embodiments, the asiRNA is a long-antisense asiRNA or lasiRNA. LasiRNAs are described, for example, in U.S. Pat. No. 9,637,742, which is hereby incorporated by reference in its entirety.

In various embodiments, the lasiRNA comprises an asiRNA with a first strand of about 21 to about 121 nt length (e.g. about 20 to about 125 nt, or about 20 to about 115 nt, or about 20 to about 105 nt, or about 20 to about 100 nt, or about 20 to about 90 nt, or about 20 to about 80 nt, or about 20 to about 70 nt, or about 20 to about 60 nt, or about 20 to about 50 nt, or about 20 to about 40 nt, or about 20 to about 30 nt, or about 30 to about 125 nt, or about 40 to about 125 nt, or about 50 to about 125 nt, or about 60 to about 125 nt, or about 70 to about 125 nt, or about 80 to about 125 nt, or about 90 to about 125 nt, or about 100 to about 125 nt, or about 24 to about 119 nt length, or about 26-31 nt length, or about 26, or about 27, or about 28, or about 29, or about 30, or about 31 nt length) comprising a region 100% complementary to a target nucleic acid, wherein the region 100% complementary to the target nucleic acid comprises the 19 most 5' nucleic acids of the first strand; and a second strand of 16 nt length that binds complementarily to the region of the first strand 100% complementary to the target nucleic acid, wherein the second strand binds to the first strand such that the first strand has a double-stranded region to which the second strand binds and a single-stranded region to which the second strand does not bind, and wherein the 5' end of the first strand and the 3' end of the second strand form a blunt end.

In various embodiments, the siRNA described herein may be composed of ribonucleotides, deoxyribonucleotides, or both, and may include a variety of modifications providing protection from nucleases or strengthening base pairing interactions. For example, the nucleic acid molecule may comprise one or more nucleotides linked by phorpohorothioate bonds, nucleotides with modifications at the 2' position, or multicyclic or locked nucleotides.

In some embodiments, the siRNA described herein can employ a variety of oligonucleotide chemistries. Examples of oligonucleotide chemistries include, without limitation, 2'O-Me-modified oligonucleotides, peptide nucleic acid (PNA), locked nucleic acid (LNA), phosphorothioate, and morpholino chemistries, and combinations of any of the foregoing.

In some embodiments, a hydroxyl group at position 2' of ribose of at least one nucleotide included in the RNAi-inducing double-stranded nucleic acid molecule (e.g., asiRNA or cp-asiRNA) is substituted with at least one selected from a hydrogen atom, a fluorine atom, an —O-alkyl group, an —O-acyl group and an amino group. In some embodiments, the phosphate backbone of at least one nucleotide, included in the nucleic acid molecule, may be substituted with at least one selected from alkylphosphonate form, phosphoroamidate form and boranophosphate form.

In some embodiments, at least one nucleotide included in the nucleic acid molecule may be substituted with at least one selected from LNA (locked nucleic acid), UNA (unlocked nucleic acid), morpholino, and PNA (peptide nucleic acid). In some embodiments, at least one of the nucleotides of the single-stranded region in the first strand may comprise a bulky base analog.

For example, in an embodiment, the nucleic acid molecule comprises one or more multicyclic or locked nucleic acids (LNA). A locked nucleic acid is a modified RNA nucleotide. The ribose moiety of a locked nucleic acid nucleotide is modified with an extra bridge connecting the 2' oxygen and 4' carbon. The bridge "locks" the ribose in the 3'-endo (North) conformation, which is often found in the A-form duplexes. Locked nucleic acid nucleotides can be mixed with DNA or RNA residues in the polynucleotide whenever desired and hybridize with DNA or RNA according to Watson-Crick base-pairing rules. The locked ribose conformation enhances base stacking and backbone pre-organization. This significantly increases the hybridization properties (melting temperature) of polynucleotides. Polynucleotides comprising locked nucleic acid nucleotides are nuclease resistant, increasing their chemical stability.

In some embodiments, the nucleic acid molecule may include one or more modified nucleotides. Exemplary modified nucleotides are described in U.S. Pat. No. 8,278,036, which is hereby incorporated by reference in its entirety. For example, the modified nucleotides may be selected from one or more of pseudouridine, N1-methylpseudouridine, 5-methylcytidine, or N6-methyladenosine, 5-hydroxycytidine, 5-hydroxymethylcytidine, 5-carboxycytidine, 5-formylcytidine, 5-hydroxyuridine, 5-hydroxymethyluridine, 5-carboxyuridine, 5-formyluridine, pseudouridine, 2-thiouridine, 4-thiouridine, 5-azauridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, N4-methylcytidine, 2-thiocytidine, 5-azacytidine, 5-aminocytidine, N4-methylpseudoisocytidine, 2-thiopseudoisocytidine, 5-hydroxypseudoisocytidine, 5-aminopseudoisocytidine, 5-methylpseudoisocytidine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine. In some embodiments, the modified oligonucleotides can be selected and placed such that they do not interfere with base pairing between the two strands of the nucleic acid molecule.

In various embodiments, the present invention provides pharmaceutical compositions comprising an siRNA, such as a cell-penetrating asymmetric small interfering RNA (cp-asiRNA) or a long-antisense asiRNA (lasiRNA); and an L-type calcium channel blocker which can enhance the cellular penetration of the siRNA, leading to more efficient gene silencing.

In various embodiments, the L-type calcium channel blocker is a dihydropyridine L-type calcium channel blocker. Exemplary dihydropyridine L-type calcium channel blocker includes, but is not limited to, amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, and pranidipine. In some embodiments, the L-type calcium channel blocker may be selected from:

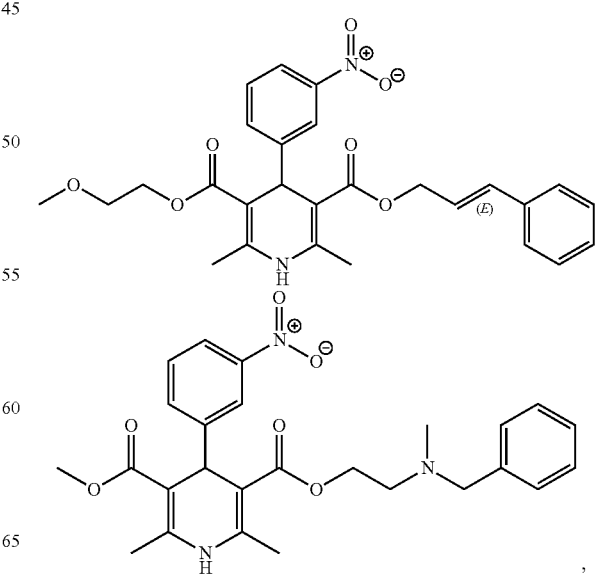

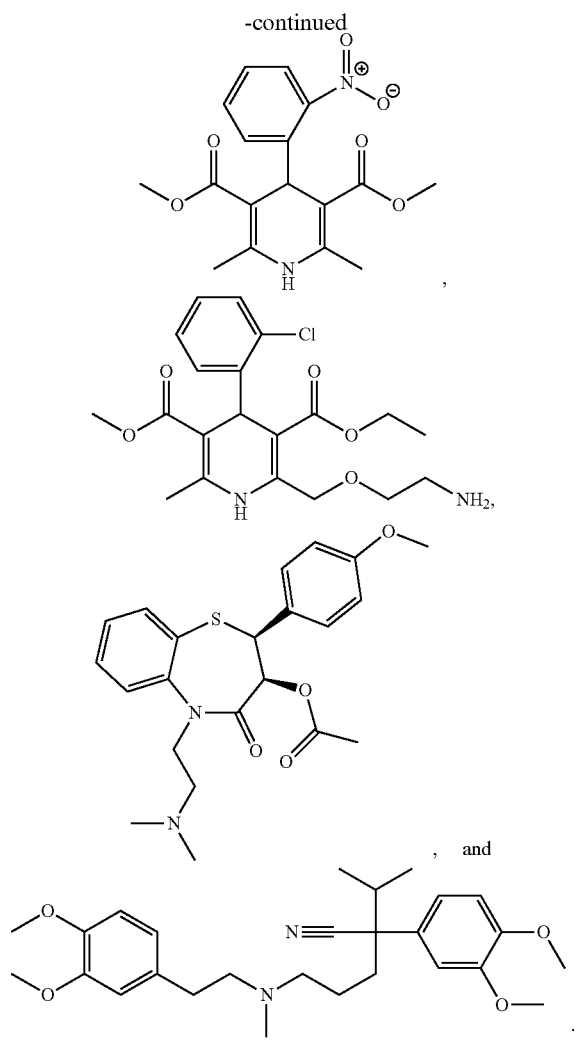

, and

In other embodiments, the L-type calcium channel blocker is a non-dihydropyridine L-type calcium channel blocker. Exemplary non-dihydropyridine L-type calcium channel blocker includes, but is not limited to, (i) phenylalkylamine and benzothiazepin calcium channel blockers including verapamil, diltiazem, gallopamil, and fendiline; (ii) gabapentinoids including gabapentin and pregabalin; (iii) zixonotide; and (iv) mibefradil, bepridil, flunarizine, and fluspirilene.

In other aspects, the invention provides a method of gene silencing in a subject, where the method comprises administering to the subject an effective amount of a small interfering RNA (siRNA); and an L-type calcium channel blocker. The siRNA and the L-type calcium channel blocker can be administered as a single pharmaceutical composition, or in some embodiments the siRNA and the L-type calcium channel blocker are administered as separate pharmaceutical compositions. In some embodiments, the siRNA is an asymmetric siRNA (asiRNA), such as a cell penetrating asiRNA (cp-asiRNA) or a long-antisense asiRNA (lasiRNA). The L-type calcium channel blocker may be a dihydropyridine L-type calcium channel blocker, or a non-dihydropyridine L-type calcium channel blocker.

Exemplary asiRNA that may be used in connection with the invention are listed in Tables 1-3 below.

TABLE 1

| No. | siRNA NAME | SEQ ID | | Sequence (5' → 3') |
|---|---|---|---|---|
| No. 1 | siRNA | 1 | sense | GCGAGGAGUGGGUGUGUGAtt |
| | | 2 | antisense | UCCUCGCAGCAUUUCCCGGtt |
| | asiRNA | 3 | sense | AGGAGUGGGUGUGUGA |
| | | 4 | antisense | UCCUCGCAGCAUUUCCCGGtt |
| | lasiRNA | 5 | sense | AGGAGUGGGUGUGUGA |
| | | 6 | antisense | UCACACACCCACUCCUCGCAG CAUUUCCCGG |
| No. 2 | siRNA | 7 | sense | AGACCUGUGGGAUGGGCAUtt |
| | | 8 | antisense | CAGGUCUUGGAACAGGCGCtt |
| | asiRNA | 9 | sense | CCUGUGGGAUGGGCAU |
| | | 10 | antisense | CAGGUCUUGGAACAGGCGCtt |
| | lasiRNA | 11 | sense | CCUGUGGGAUGGGCAU |
| | | 12 | antisense | AUGCCCAUCCCACAGGUCUUG GAACAGGCGC |
| No. 3 | siRNA | 13 | sense | ACAGGAAGAUGUACGGAGAtt |
| | | 14 | antisense | UUCCUGUAGUACAGCGAUUtt |
| | asiRNA | 15 | sense | GGAAGAUGUACGGAGA |
| | | 16 | antisense | UUCCUGUAGUACAGCGAUUtt |
| | lasiRNA | 17 | sense | GGAAGAUGUACGGAGA |
| | | 18 | antisense | UCUCCGUACAUCUUCCUGUAG UACAGCGAUU |
| No. 4 | siRNA | 19 | sense | GCACCAGCAUGAAGACAUAtt |
| | | 20 | antisense | UAUGUCUUCAUGCUGGUGCtt |
| | asiRNA | 21 | sense | CCAGCAUGAAGACAUA |
| | | 22 | antisense | UAUGUCUUCAUGCUGGUGCtt |
| | lasiRNA | 23 | sense | CCAGCAUGAAGACAUA |
| | | 24 | antisense | UAUGUCUUCAUGCUGGUCCAG CCAGAAAGCU |
| No. 5 | siRNA | 25 | sense | GAAGACAUACCGAGCUAAAtt |
| | | 26 | antisense | UUUAGCUCGGUAUGUCUUCtt |
| | asiRNA | 27 | sense | GACAUACCGAGCUAAA |
| | | 28 | antisense | UUUAGCUCGGUAUGUCUUCtt |
| | lasiRNA | 29 | sense | GACAUACCGAGCUAAA |
| | | 30 | antisense | UUUAGCUCGGUAUGUCUUCAU GCUGGUGCAG |
| No. 6 | siRNA | 31 | sense | GCUAAAUUCUGUGGAGUAUtt |
| | | 32 | antisense | AUACUCCACAGAAUUUAGCtt |
| | asiRNA | 33 | sense | AAAUUCUGUGGAGUAU |
| | | 34 | antisense | AUACUCCACAGAAUUUAGCtt |
| | lasiRNA | 35 | sense | AAAUUCUGUGGAGUAU |
| | | 36 | antisense | AUACUCCACAGAAUUUAGCUC GGUAUGUCUU |
| No. 7 | siRNA | 37 | sense | GCGAGGUCAUGAAGAAGAAtt |
| | | 38 | antisense | UUGUUCUUCAUGACCUCGCtt |
| | asiRNA | 39 | sense | AGGUCAUGAAGAAGAA |
| | | 40 | antisense | UUGUUCUUCAUGACCUCGCtt |
| | lasiRNA | 41 | sense | AGGUCAUGAAGAAGAA |
| | | 42 | antisense | UUGUUCUUCAUGACCUCGCCG UCAGGGCACU |
| No. 8 | siRNA | 43 | sense | UGGAAGAGAACAUUAAGAAtt |
| | | 44 | antisense | UUCUUAAUGUUCUCUUCCAtt |

TABLE 1-continued

| No. | siRNA NAME | SEQ ID | | Sequence (5' → 3') |
|---|---|---|---|---|
| | asiRNA | 45 | sense | AAGAGAACAUUAAGAA |
| | | 46 | antisense | UUCUUAAUGUUCUCUUCCAtt |
| | lasiRNA | 47 | sense | AAGAGAACAUUAAGAA |
| | | 48 | antisense | UUCUUAAUGUUCUCUUCCAGGUCAGCUUCGC |

(Capital letters: RNA, small letters: DNA)

TABLE 2

| No. | siRNA NAME | SEQ ID | | Sequence (5' → 3') |
|---|---|---|---|---|
| No. 9 | siRNA | 49 | sense | CGGCUUACCGACUGGAAGAtt |
| | | 50 | antisense | UCUUCCAGUCGGUAAGCCGtt |
| | asiRNA | 51 | sense | CUUACCGACUGGAAGA |
| | | 52 | antisense | UCUUCCAGUCGGUAAGCCGtt |
| | lasiRNA | 53 | sense | CUUACCGACUGGAAGA |
| | | 54 | antisense | UCUUCCAGUCGGUAAGCCGCGAGGGCAGGCC |
| No. 10 | siRNA | 55 | sense | GCAUGAAGCCAGAGAGUGAtt |
| | | 56 | antisense | UCACUCUCUGGCUUCAUGCtt |
| | asiRNA | 57 | sense | UGAAGCCAGAGAGUGA |
| | | 58 | antisense | UCACUCUCUGGCUUCAUGCtt |
| | lasiRNA | 59 | sense | UGAAGCCAGAGAGUGA |
| | | 60 | antisense | UCACUCUCUGGCUUCAUGCCCAUGUCUCCGU |
| No. 11 | siRNA | 61 | sense | CACCAUAGGUAGAAUGUAAtt |
| | | 62 | antisense | UUACAUUCUACCUAUGGUGtt |
| | asiRNA | 63 | sense | CAUAGGUAGAAUGUAA |
| | | 64 | antisense | UUACAUUCUACCUAUGGUGtt |
| | lasiRNA | (65 | sense | CAUAGGUAGAAUGUAA |
| | | 66 | antisense | UUACAUUCUACCUAUGGUGUUCAGAAAUUGA |
| No. 12 | siRNA | 67 | sense | CCUGCAGGCUAGAGAAGCAtt |
| | | 68 | antisense | UGCUUCUCUAGCCUGCAGGtt |
| | asiRNA | 69 | sense | GCAGGCUAGAGAAGCA |
| | | 70 | antisense | UGCUUCUCUAGCCUGCAGGtt |
| | lasiRNA | 71 | sense | GCAGGCUAGAGAAGCA |
| | | 72 | antisense | UGCUUCUCUAGCCUGCAGGAGGCGUUGUCAU |
| No. 13 | siRNA | 73 | sense | CCAGAGAGUGAGAGACAUUtt |
| | | 74 | antisense | AAUGUCUCUCACUCUCUGGtt |
| | asiRNA | 75 | sense | GAGAGUGAGAGACAUU |
| | | 76 | antisense | AAUGUCUCUCACUCUCUGGtt |
| | lasiRNA | 77 | sense | GAGAGUGAGAGACAUU |
| | | 78 | antisense | AAUGUCUCUCACUCUCUGGCUUCAUGCCAUG |
| No. 14 | siRNA | 79 | sense | GCGAAGCUGACCUGGAAGAtt |
| | | 80 | antisense | UCUUCCAGGUCAGCUUCGCtt |
| | asiRNA | 81 | sense | AAGCUGACCUGGAAGA |
| | | 82 | antisense | UCUUCCAGGUCAGCUUCGCtt |
| | lasiRNA | 83 | sense | AAGCUGACCUGGAAGA |
| | | 84 | antisense | UCUUCCAGGUCAGCUUCGCAGGCCUGACCA |

TABLE 2-continued

| No. | siRNA NAME | SEQ ID | | Sequence (5' → 3') |
|---|---|---|---|---|
| No. 15 | siRNA | 85 | sense | CCGGAGACAAUGACAUCUUtt |
| | | 86 | antisense | AAGAUGUCAUUGUCUCCGGtt |
| | asiRNA | 87 | sense | GAGACAAUGACAUCUU |
| | | 88 | antisense | AAGAUGUCAUUGUCUCCGGtt |
| | lasiRNA | 89 | sense | GAGACAAUGACAUCUU |
| | | 90 | antisense | AAGAUGUCAUUGUCUCCGGGACAGUUGUAAU |
| No. 16 | siRNA | 91 | sense | UCUUUGAAUCGCUGUACUAtt |
| | | 92 | antisense | UAGUACAGCGAUUCAAAGAtt |
| | asiRNA | 93 | sense | UUGAAUCGCUGUACUA |
| | | 94 | antisense | UAGUACAGCGAUUCAAAGAtt |
| | lasiRNA | 95 | sense | UUGAAUCGCUGUACUA |
| | | 96 | antisense | UAGUACAGCGAUUCAAAGAUGUCAUUGUCUC |

(Capital letters: RNA; small letters: DNA)

TABLE 3

| No. | siRNA NAME | SEQ ID | | Sequence (5' → 3') |
|---|---|---|---|---|
| No. 17 | siRNA | 97 | sense | UUGCGAAGCUGACCUGGAAtt |
| | | 98 | antisense | UUCCAGGUCAGCUUCGCAAtt |
| | asiRNA | 99 | sense | CGAAGCUGACCUGGAA |
| | | 100 | antisense | UUCCAGGUCAGCUUCGCAAtt |
| | lasiRNA | 101 | sense | CGAAGCUGACCUGGAA |
| | | 102 | antisense | UUCCAGGUCAGCUUCGCAAGGCCUGACCAUG |
| No. 18 | siRNA | 103 | sense | CAACUAUGAUUAGAGCCAAtt |
| | | 104 | antisense | UUGGCUCUAAUCAUAGUUGtt |
| | asiRNA | 105 | sense | CUAUGAUUAGAGCCAA |
| | | 106 | antisense | UUGGCUCUAAUCAUAGUUGtt |
| | lasiRNA | 107 | sense | CUAUGAUUAGAGCCAA |
| | | 108 | antisense | UUGGCUCUAAUCAUAGUUGGGUCUGGGCCAA |
| No. 19 | siRNA | 109 | sense | GUACCAGUGCACGUGCCUGtt |
| | | 110 | antisense | CAGGCACGUGCACUGGUACtt |
| | asiRNA | 111 | sense | CCAGUGCACGUGCCUG |
| | | 112 | antisense | CAGGCACGUGCACUGGUACtt |
| | lasiRNA | 113 | sense | CCAGUGCACGUGCCUG |
| | | 114 | antisense | CAGGCACGUGCACUGGUACUUGCAGCUGCUC |
| No. 20 | siRNA | 115 | sense | AGUGCAUCCGUACUCCCAAtt |
| | | 116 | antisense | UUGGGAGUACGGAUGCACUtt |
| | asiRNA | 117 | sense | GCAUCCGUACUCCCAA |
| | | 118 | antisense | UUGGGAGUACGGAUGCACUtt |
| | lasiRNA | 119 | sense | GCAUCCGUACUCCCAA |
| | | 120 | antisense | UUGGGAGUACGGAUGCACUUUUGCCCUUCU |
| No. 21 | siRNA | 121 | sense | CAUGAUGUUCAUCAAGACCtt |
| | | 122 | antisense | GGUCUUGAUGAACAUCAUGtt |
| | asiRNA | 123 | sense | GAUGUUCAUCAAGACC |
| | | 124 | antisense | GGUCUUGAUGAACAUCAUGtt |

TABLE 3-continued

| siRNA No. | siRNA NAME | SEQ ID | | Sequence (5' → 3') |
|---|---|---|---|---|
| | lasiRNA | 125 | sense | GAUGUUCAUCAAGACC |
| | | 126 | antisense | GGUCUUGAUGAACAUCAUGUU CUUCUUCAUG |
| No. 22 | siRNA | 127 | sense | CCAUGACCGCCGCCAGUAUtt |
| | | 128 | antisense | AUACUGGCGGCGGUCAUGGtt |
| | asiRNA | 129 | sense | UGACCGCCGCCAGUAU |
| | | 130 | antisense | AUACUGGCGGCGGUCAUGGtt |
| | lasiRNA | 131 | sense | UGACCGCCGCCAGUAU |
| | | 132 | antisense | AUACUGGCGGCGGUCAUGGUU GGCACUGCGG |
| No. 23 | siRNA | 133 | sense | GAACAUUAAGAAGGGCAAAtt |
| | | 134 | antisense | UUUGCCCUUCUUAAUGUUCtt |
| | asiRNA | 135 | sense | CAUUAAGAAGGGCAAA |
| | | 136 | antisense | UUUGCCCUUCUUAAUGUUCtt |
| | lasiRNA | 137 | sense | CAUUAAGAAGGGCAAA |
| | | 138 | antisense | UUUGCCCUUCUUAAUGUUCUC UUCCAGGUCA |
| No. 24 | siRNA | 139 | sense | GGAAGACACGUUUGGCCCAtt |
| | | 140 | antisense | UGGGCCAAACGUGUCUUCCtt |
| | asiRNA | 141 | sense | AGACACGUUUGGCCCA |
| | | 142 | antisense | UGGGCCAAACGUGUCUUCCtt |
| | lasiRNA | 143 | sense | AGACACGUUUGGCCCA |
| | | 144 | antisense | UGGGCCAAACGUGUCUUCCAG UCGGUAAGCC |

(Capital letters: RNA; small letters: DNA)

In various embodiments, the present invention provides methods for gene silencing of a target gene. In various embodiments, the target gene may be selected from mRNA (messenger RNA), microRNA, piRNA (piwi-interacting RNA), a coding DNA sequence, and a non-coding DNA sequence. In some embodiments, the target gene is mRNA. In additional embodiments, the target gene is mRNA encoding a connective tissue growth factor (CTGF).

In another aspect, the present disclosure further provides methods of screening for a compound to improve, increase or enhance an activity of an siRNA (e.g., asi-RNA or cp-asiRNA or lasiRNA) comprising contacting the siRNA with a cell; contacting a candidate compound with the cell and/or the siRNA; and detecting the siRNA penetrated into the cell. In some embodiments, the method further comprises comparing an amount of siRNA (e.g., asi-RNA or cp-asiRNA or lasiRNA) penetrated into the cell with a control to determine whether the penetration of the siRNA into the cell with the candidate compound is increased compared to that without the candidate compound. In some embodiments, the control may be an experimented, known or estimated amount of the siRNA (e.g., asi-RNA or cp-asiRNA or lasiRNA) penetrated without any secondary compound to improve, increase or enhance the cell penetrating activity of the siRNA. The control may be a known value or a predetermined value from a previous experiment. The method may further comprise selecting the candidate compound that increases penetrating of an siRNA (e.g., asi-RNA or cp-asiRNA or lasiRNA) into the cell as the compound to improve the activity of the siRNA.

In additional embodiments, the method described herein further comprises detecting a gene-silencing activity of an siRNA (e.g., asi-RNA or cp-asiRNA or lasiRNA) in the cell. The candidate compound that increases the gene-silencing activity of the siRNA (e.g., asi-RNA or cp-asiRNA or lasiRNA) in the cell may be selected as the compound to improve the activity of the siRNA. In further embodiments, the method further comprises comparing a gene-silencing activity of the siRNA (e.g., asi-RNA or cp-asiRNA or lasiRNA) with a control to determine whether the gene-silencing activity of the siRNA with the candidate compound is increased compared to that without the candidate compound. The control may be an experimented, known or estimated gene-silencing activity of the siRNA (e.g., asi-RNA or cp-asiRNA or lasiRNA) without any secondary compound to improve, increase or enhance the gene-silencing activity of the siRNA. The control may be a known value or a predetermined value from a previous experiment.

In various embodiments, the method further comprises preparing a cell culture comprising the cell on a substrate. In some embodiments, the method comprises preparing a cell culture comprising the cell on a plurality of discrete substrates. In some embodiments, the cell on the substrate is contacted with an siRNA (e.g., asi-RNA or cp-asiRNA or lasiRNA) or a combination of siRNAs. For example, the cell on the substrate may contact a first siRNA (e.g., asi-RNA or cp-asiRNA or lasiRNA) or a first combination of siRNAs (e.g., asi-RNAs or cp-asiRNAs or lasiRNA) and a second siRNA (e.g., asi-RNA or cp-asiRNA or lasiRNA) or a second combination of siRNAs (e.g., asi-RNAs or cp-asiRNAs or lasiRNA). In some embodiments, the first siRNA or the first combination of siRNAs contacting the cell on one of the plurality of discrete substrates may be different from the second siRNA or the second combination of siRNAs contacting the cell on another one of the plurality of discrete substrates. A cell on each of the plurality of discrete substrates may contact a different siRNA or combination of siRNAs. In some embodiments, the method comprises comprising contacting a plurality of candidate compounds with the cell on a plurality of substrates, and simultaneously incubating the plurality of candidate compounds with the cell. In additional embodiments, the method comprises simultaneously contacting a plurality of candidate compounds with the cell on a plurality of substrates. In some embodiments, the substrate is a well. In some embodiments, the cell is a human cell.

In some embodiments, the siRNA (e.g., asi-RNA or cp-asiRNA or lasiRNA) is labeled, for example, with a fluorescent dye. The siRNA (e.g., asi-RNA or cp-asiRNA or lasiRNA) may be detected, for example, by detecting the label. The amount of siRNA (e.g., asi-RNA or cp-asiRNA or lasiRNA) may be determined, for example, by measuring the amount of the label.

In various embodiments, the present invention provides pharmaceutical compositions which are formulated for various delivery routes, including rectal, buccal, intranasal and transdermal routes, by intra-arterial injection, intravenously, intraperitoneally, parenterally, intramuscularly, subcutaneously, orally, topically, or as an inhalant. In some embodiments, the delivery routes are topical, pulmonary, or parenteral, for use in various methods of treatment as described elsewhere herein. In some embodiments, one or both of the siRNA and L-type calcium channel blocker are formulated for topical, pulmonary, or parenteral delivery. In some embodiments, the pharmaceutical composition is formulated for application to the skin, eyes, lungs, or systemic delivery. In various embodiments, the pharmaceutical compositions are used for in vitro and/or in vivo delivery together with various delivery vehicles, such as, without limitation, liposomes, cationic polymers, antibodies, aptamers or nanoparticles.

In some embodiments, the pharmaceutical compositions described herein may be a pharmaceutical composition for oral administration containing the siRNA (e.g., asi-RNA or cp-asiRNA or lasiRNA) and the L-type calcium channel blocker, and optionally a pharmaceutical excipient suitable for oral administration. In some embodiments, the pharmaceutical composition may exclude a separate delivery vehicle for the siRNA (e.g., asi-RNA or cp-asiRNA or lasiRNA). In various embodiments, the pharmaceutical composition is formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like.

In some embodiments, the pharmaceutical compositions described herein may be a pharmaceutical composition for injection containing the siRNA (e.g., asi-RNA or cp-asiRNA or lasiRNA) and the L-type calcium channel blocker described herein, and optionally a pharmaceutical excipient suitable for injection. In some embodiments, the pharmaceutical composition may exclude a separate delivery vehicle for the siRNA (e.g., asi-RNA or cp-asiRNA or lasiRNA).

In some embodiments, the forms in which the pharmaceutical compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. In some embodiments, aqueous solutions in saline are used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, and in the case of dispersion, by the use of surfactants. The pharmaceutical composition can further comprise various antibacterial and antifungal agents, for example, parabens, chlorobutanol, phenol, sorbic acid and thimerosal.

Sterile injectable solutions are prepared by incorporating an active pharmaceutical ingredient or combination of active pharmaceutical ingredients in the required amounts in the appropriate solvent with various other ingredients as enumerated above, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the pharmaceutical compositions are administered topically to body surfaces and are thus formulated in a form suitable for topical administration. Suitable topical formulations include, without limitation, gels, ointments, creams, lotions, drops and the like.

In various embodiments, the pharmaceutical composition of the invention further includes a pharmaceutically acceptable carrier or diluent. Pharmaceutically acceptable carriers or diluents are well known to those skilled in the art. The carrier or diluent may be, in various embodiments, a solid carrier or diluent for solid formulations, a liquid carrier or diluent for liquid formulations, or mixtures thereof. In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In some embodiment, the pharmaceutical compositions are controlled-release compositions, i.e. compositions in which the active agents are released over a period of time after administration. Controlled- or sustained-release compositions include formulation in lipophilic depots (e.g. fatty acids, waxes, oils). In another embodiment, the composition is an immediate-release composition, i.e. a composition in which the active agents are released immediately after administration.

In various embodiments, the siRNA (e.g., asi-RNA or cp-asiRNA or lasiRNA) and the L-type calcium channel blocker described herein are co-administered as a pharmaceutical composition. The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration may include simultaneous or time-separated administration in different compositions, administration at different times in separate compositions, or administration in a pharmaceutical composition in which two or more active pharmaceutical ingredients are present. Simultaneous administration in separate compositions and administration in a pharmaceutical composition in which both agents are present is also encompassed in the methods of the invention.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the oral route, may be used as appropriate. A single dose of a pharmaceutical composition may also be used for treatment of an acute condition. In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

In another aspect, the disclosure is related to a method of gene silencing in a subject, comprising administering to the subject an effective amount of the pharmaceutical composition described herein. The methods of gene silencing using siRNA (e.g., asi-RNA or cp-asiRNA or lasiRNA) are described at least in U.S. Patent Application Publication Nos. 2017/0137828 and 2017/0027837, all of which are incorporated herein by reference in their entirety.

In some embodiments, the present disclosure is related to a method of treating or preventing a connective tissue growth factor (CTGF)-associated disease or disorder in a subject, comprising administering to the subject an effective amount of the pharmaceutical composition comprising an siRNA (e.g., asi-RNA or cp-asiRNA or lasiRNA) and/or a L-type calcium channel blocker as described herein. In some embodiments, the siRNA (e.g., asi-RNA or cp-asiRNA or lasiRNA) comprises an antisense strand of at least 19 nucleotides in length having a sequence complementarity to CTGF-encoding mRNA and a sense strand of 15 to 17 nucleotides in length having a sequence complementarity to the antisense strand. In various embodiments, the CTGF-associated disease or disorder may be selected from keloid, kidney fibrosis, pachydermatosis, pulmonary fibrosis, hepatic fibrosis, arthritis, hypertension, renal failure, vasculogenesis-related disorder, dermatofibrosis, and cardiovascular system disorder. In some embodiments, the siRNA (e.g., asi-RNA or cp-asiRNA or lasiRNA) may be conjugated to a lipophilic compound and has a pair of nucleic sequences selected from a pair of nucleotide sequences of SEQ ID NOs: 1 and 2, a pair of nucleotide sequences of SEQ ID NOs: 3 and 4, and a pair of nucleotide sequences of SEQ ID NOs: 5 and 6. Additional siRNAs (e.g., asi-RNAs or cp-asiRNAs or lasiRNA) that may be utilized for treating or preventing a CTGF-associated disease or disorder are disclosed in U.S. Patent Publication No. 20150111948, the entire disclosure of which is hereby incorporated by reference.

In some embodiments, the present disclosure is related to a method of treating an ocular condition such as age-related macular degeneration (AMD; e.g., dry or wet AMD) in a subject in need thereof, comprising administering to the subject an effective amount of the pharmaceutical composition described herein, wherein the siRNA (e.g., asi-RNA or cp-asiRNAs or lasiRNA) comprises an antisense strand of at least 19 nucleotides in length having sequence complementarity to a MyD88 mRNA sequence or a TLR3 mRNA sequence and a sense strand of 15 to 17 nucleotides in length having sequence complementarity to the antisense strand, wherein the antisense strand and the sense strand form a complex in which the 5' end of the antisense strand and the 3' end of the sense strand form a blunt end. Exemplary siRNAs (e.g., asi-RNAs or cp-asiRNAs or lasiRNA) that may be utilized for treating or preventing AMD are disclosed in U.S. Patent Publication No. 20170137828, the entire disclosure of which is hereby incorporated by reference.

In some embodiments, the present disclosure is related to a method of inhibiting and/or reducing melanin production in a subject, comprising administering to the subject an effective amount of the pharmaceutical composition described herein, wherein the siRNA (e.g., asi-RNA or cp-asiRNA) comprises an antisense strand of at least 19 nucleotides in length having sequence complementarity to a tyrosinase mRNA sequence and a sense strand of 15 to 17 nucleotides in length having sequence complementarity to the antisense strand, wherein the antisense strand and the sense strand form a complex in which the 5' end of the antisense strand and the 3' end of the sense strand form a blunt end. Exemplary siRNAs (e.g., asi-RNAs or cp-asiRNAs or lasiRNA) that may be utilized for inhibiting and/or reducing melanin production are disclosed in U.S. Patent Publication No. 20170027837, the entire disclosure of which is hereby incorporated by reference. In some embodiments, the present disclosure further provides methods of treating skin diseases or conditions including, but are not limited to, skin whitening, darkening, or scarring, atopic dermatitis, psoriasis, scleroderma, hair loss, or wrinkled skin.

In various embodiments, the subject being treated by methods of the invention is human.

EXAMPLES

The embodiments encompassed herein are now described with reference to the following examples. These examples are provided for the purpose of illustration only and the disclosure should in no way be construed as being limited to these examples, but rather should be construed to encompass any and all variations which become evident as a result of the teachings provided herein.

Example 1. High-Throughput Screening for Improvement of Cp-asiRNA Gene Silencing Activity After DMSO toxicity test, 2354 clinical active candidate compounds from a chemical library in Korea Chemical Bank were diluted in distilled water and stored in 96 well sealed plates. Before incubation of cp-asiGFP and chemicals, 4,000 cells of HeLa/GFP stable cell line were seeded in a 96 well plate. After 24 hours of seeding, cp-asiRNA was transfected. After 24 hours of transfection without any transfection reagent, such as lipofectamine or lipofectamine 2000, medium was changed from Opti-MEM (Gibco) to DMEM (Gibco) with 10% FBS (Gibco). Relative fluorescence intensity of cp-asiRNA with chemicals was measured using a multi-well plate reader (FIG. 1). At the first screening, relative fluorescence intensity was measured for each chemical twice. Based on first screening, five candidate chemicals with the highest intensities in each plate were selected, and a second screening was performed. The secondary screening resulted in 10 hit compounds. After analyzing the structure of the 10 compounds, 3 of the hit compounds shared a core structure and function as L-type calcium channel blocker.

Figure 2:
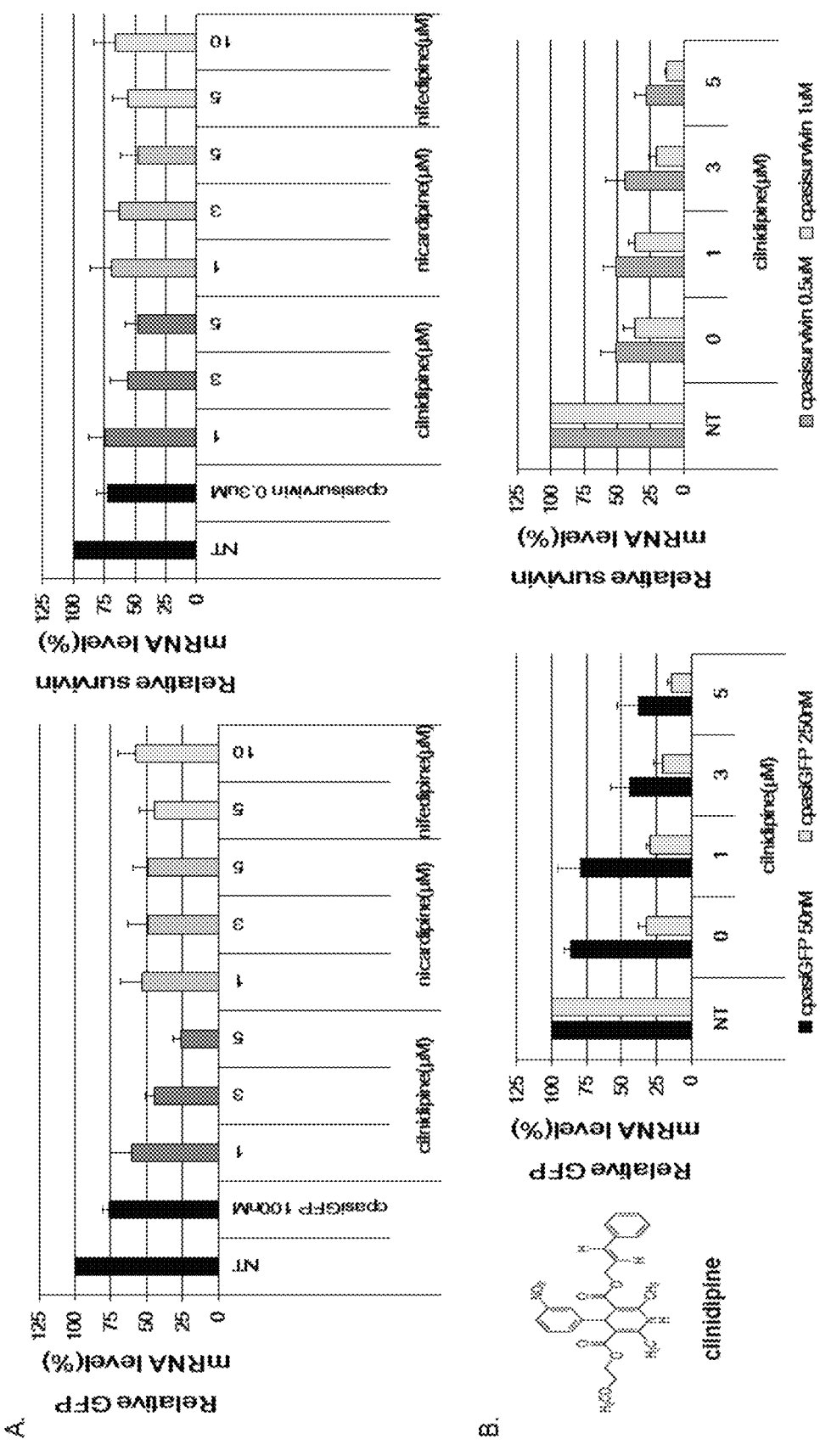
FIG. 2 illustrates enhanced gene silencing efficacy of cp-asiRNAs through 3 hit compounds identified by screening. Panel (A): Validation of the enhanced gene silencing potency by 3 hit compounds. Panel (B): Further analysis of the enhanced gene silencing potency by cilnidipine. All data in the graph represent the mean±SD of 3 independent experiments.

Example 2. Small Molecules Identified by Screening Improve the Gene Silencing of Cp-asiRNAs Three hit compounds confirmed by screening were retested to verify the RNA interference effect on cp-asiR-NAs. To set the optimal range which is not influenced by cell toxicity, MTT assay was performed. Based on this range (Lethal Dose 50), concentrations of the 3 hit compounds were selected, and the compounds retested within the selected ranges. HeLa/GFP cells were treated with Cp-asiGFPs (100 nM) and the 3 candidate chemicals. After 24 hours of incubation, medium was changed from Opti-MEM (Gibco) to DMEM (Gibco) with 10% FBS (Gibco). After 24 hours of medium change, relative GFP mRNA levels were measured using quantitative real-time reverse transcription-polymerase chain reaction (qRT-PCR) (Panel A in FIG. 2). When treated with the 3 chemicals, enhancement of cp-asiGFP activity was observed compared with cp-asiGFP alone. To test whether the gene silencing activity of cp-asiRNA is sequence specific, another cp-asiRNA targeting survivin (0.3 µM) was also tested. Cp-asisurvivin with the 3 candidate chemicals were added to HeLa cells and target mRNA levels were analyzed by qRT-PCR (Panel A in FIG. 2). The GFP and Survivin mRNA levels were calculated by dividing by the Tubulin levels as an internal control. This result showed that the gene silencing activity of cp-asisurvivin was enhanced by treating with the 3 candidate compounds.

Cilnidipine, which showed the most gene silencing effect on cp-asiRNAs, was selected. cp-asiRNA targeting GFP (50 nM and 250 nM) and cp-asiRNA targeting Survivin (0.5 µM and 1 µM) with varying concentrations of cilnidipine were added to HeLa/GFP and HeLa cells. After 48 hours, activities of cp-asiRNAs with cilnidipine were analyzed using quantitative real-time reverse transcription-polymerase chain reaction (qRT-PCR). The relative GFP and Survivin mRNA levels were measured by dividing the Tubulin levels (internal control) (Panel B in FIG. 2). Concentration-dependent enhancement of cp-asiRNA activity was observed. These results demonstrate that the 3 hit compounds identified by screening enhance the gene silencing activity of cp-asiRNAs.

Figure 3:
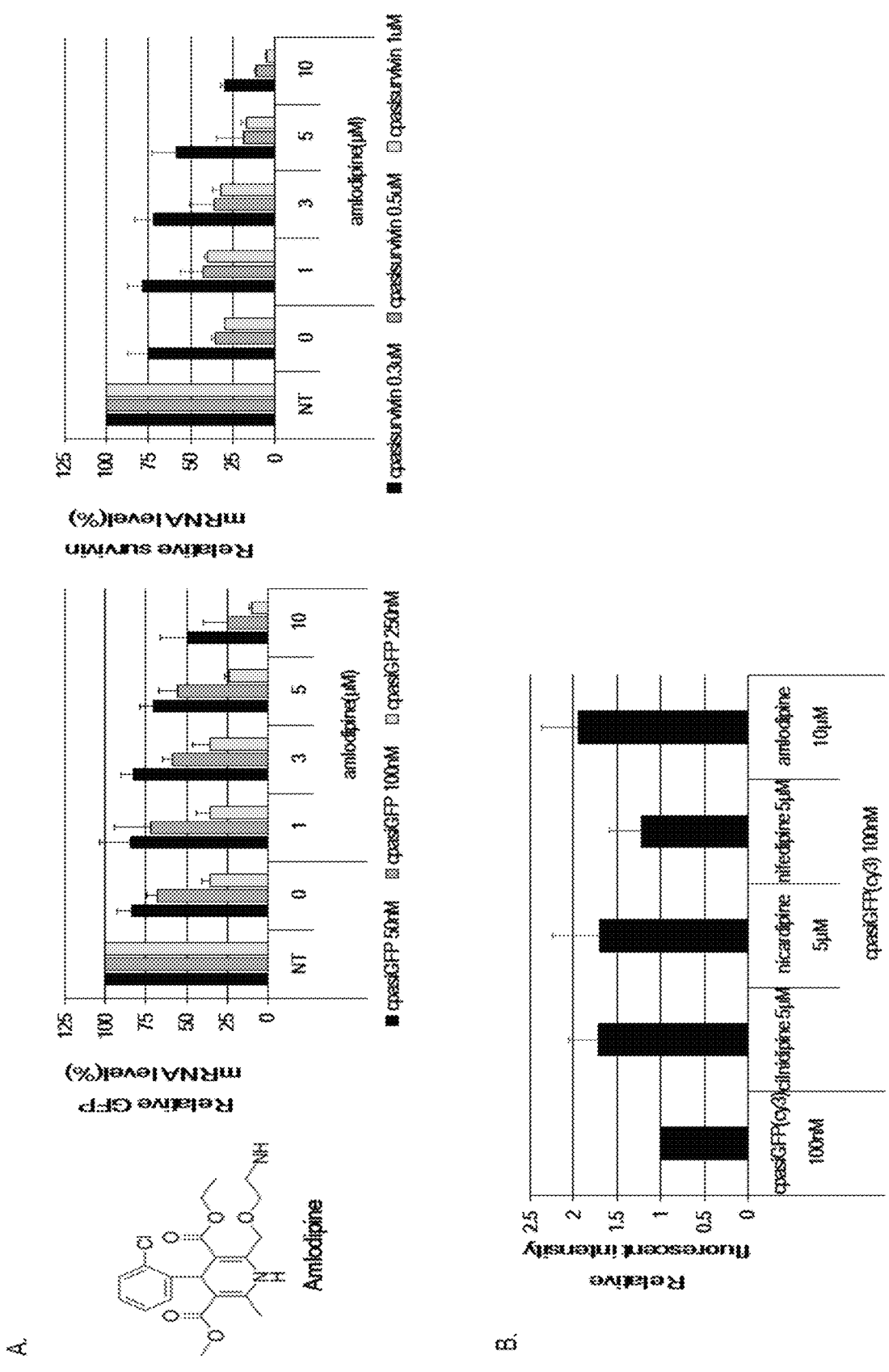
FIG. 3 illustrates the effect of DHP (Dihydropyridine) L-type calcium channel blocker. Panel (A): Analysis of the gene silencing activity by Amlodipine derived from DHP L-type calcium channel blocker. Panel (B): Nucleocounter (NC-3000) based quantification of cellular uptake by DHP L-type calcium channel blocker. All data in the graph represent the mean±SD of 3 independent experiments.

Example 3. Dihyropyridine (DHP) L-Type Calcium Channel Blocker Improves the Gene Silencing of Cp-asiRNAs Amlodipine which was not contained in the chemical library was also tested. This compound has a common structure with DHP and functions as L-type calcium channel blocker. Cp-asiGFP and cp-asisurvivin were treated with Amlodipine into HeLa/GFP and HeLa cells. Their gene silencing effect was measured by qRT-PCR after 48 hours incubation (Panel A in FIG. 3). The GFP and Survivin mRNA levels were calculated by dividing by the Tubulin levels (internal control). Reduced GFP and Survivin mRNA expression level was shown by incubation with cp-asiGFP (50 nM, 100 nM, 250 nM) and cp-asisurvivin (0.3 µM, 0.5 µM, 1 µM) with varying concentrations of Amlodipine. These results show that Amlodipine also reduces the relative target mRNA level, and enhances the gene silencing effect of cp-asiRNAs in a dose-dependent manner. The results support that RNAi efficacy of cp-asiRNAs is enhanced by not only the 3 chemical compounds identified through the screen, but also DHP L-type calcium channel blocker. Continually, Nucleocounter (NC3000) based technique was performed using Cy3 labeled cp-asiGFP to determine whether DHP L-type calcium channel blocker affects the cellular uptake (Panel B in FIG. 3). HeLa cells were treated with 100 nM Cy3 labeled cp-asiGFP with DHP L-type calcium channel blockers. After 8 hours of incubation, Hoechst 33342 (Biotium) was used for fixed and live cell fluorescent staining of DNA and nuclei. Relative fluorescent intensity was quantified compared to the intracellular fluorescent intensity on a gated cell population. The fluorescent intensity was quantified by Nucleocounter method based on intracellular Cy3 signals. The normalized fluorescent intensity was calculated relative to Cy3 labeled cp-asiGFP expression shown as 1. The cellular uptake of the cp-asiGFP with DHP L-type calcium channel blocker was higher than that of cp-asiGFP alone. The results support that DHP L-type calcium channel blocker enhances the cellular uptake, resulting in increasing the gene silencing efficacy of cp-asiRNAs.

Figure 4:
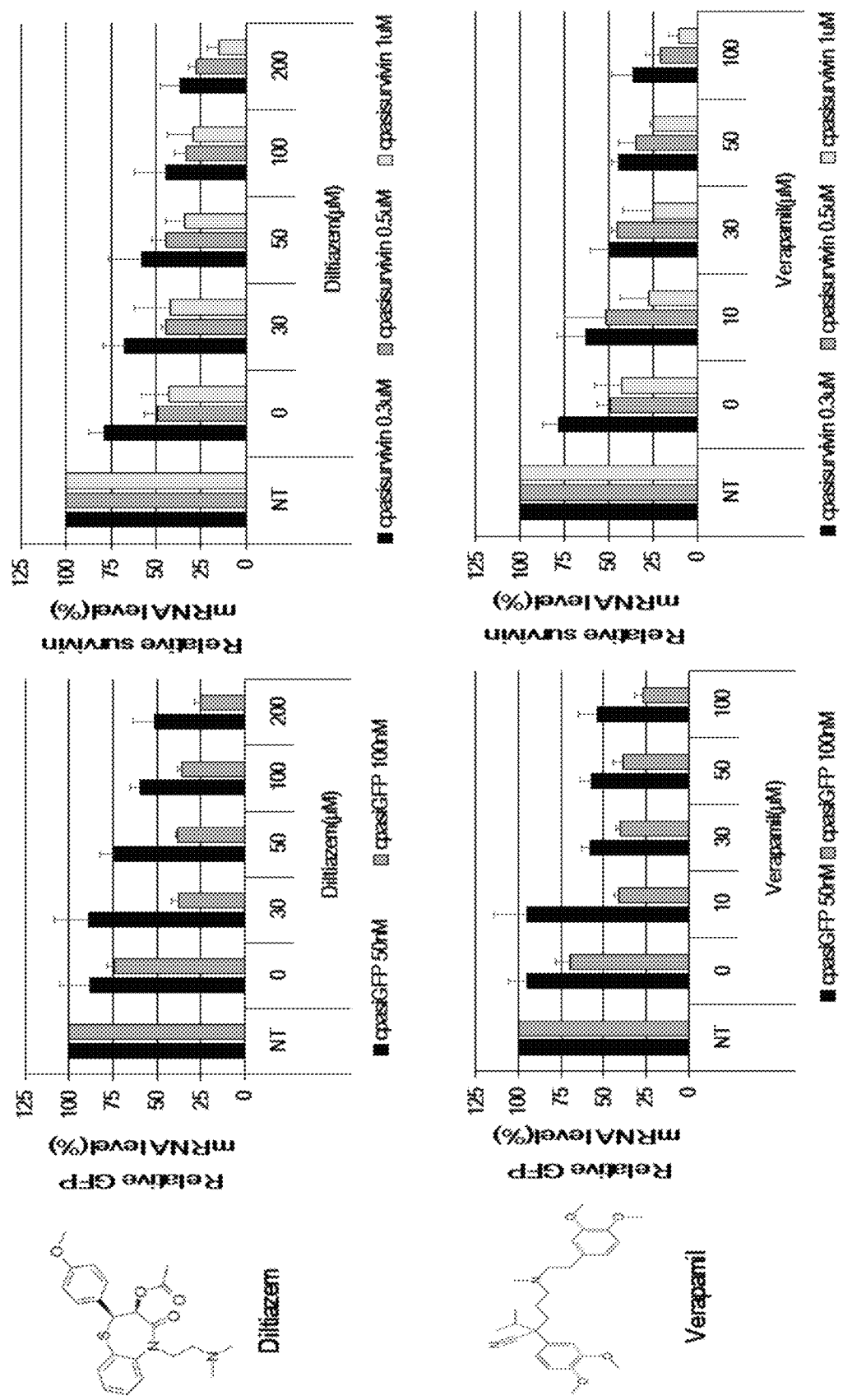
FIG. 4 illustrates gene silencing efficacy of cp-asiRNAs by non-DHP L-type calcium channel blocker. All data in the graph represent the mean±SD of 3 independent experiments.

Example 4. Non-Dihyropyridine (Non-DHP) L-Type Calcium Channel Blockers Also Improve the Gene Silencing of Cp-asiRNAs Another type of calcium channel blocker, like non-DHP L-type calcium channel blocker, is selected for testing. Cp-asiGFP and cp-asisurvivin with Diltiazem and Verapamil were treated into HeLa/GFP and HeLa cells. After 48 hours treated with cp-asiGFP (50 nM, 100 nM) and cp-asisurvivin (0.3 µM, 0.5 µM, 1 µM) with Diltiazem and Verapamil by concentration, reduced GFP and Survivin mRNA levels were observed using quantitative real-time reverse transcription-polymerase chain reaction (qRT-PCR). The GFP and Survivin mRNA levels were calculated divided by the Tubulin levels as an internal control. As seen FIG. 4, when treated with Diltiazem and Verapamil, the gene silencing efficacy of cp-asiRNAs was more efficient than treatment with cp-asiRNAs alone. Thus, these 2 compounds also show similar effect on cp-asiRNAs compared with the DHP L-type calcium channel blocker, confirming that the enhanced gene silencing effect is influenced by the L-type calcium channel blocker.

Figure 5:
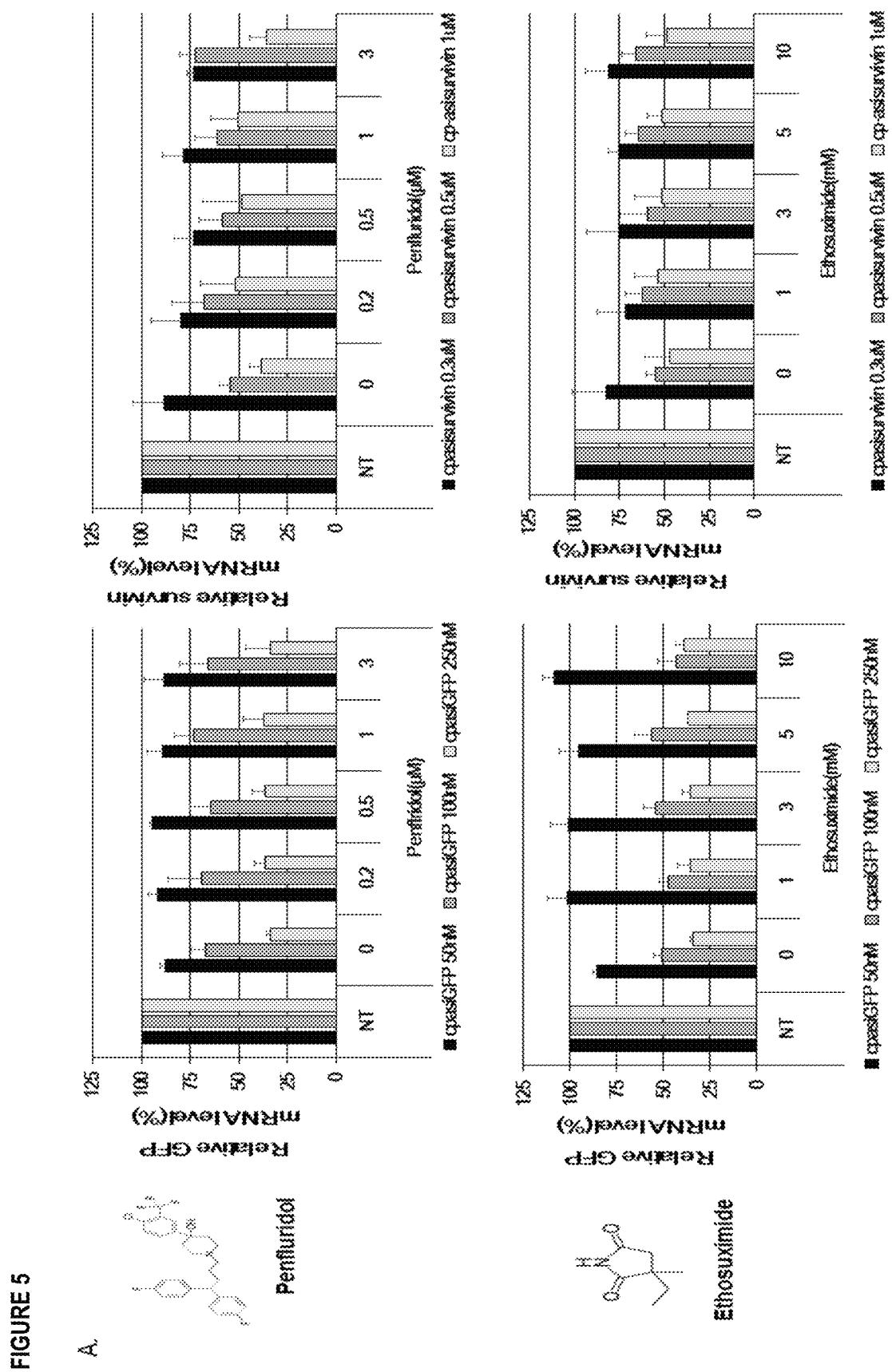
FIG. 5 illustrates the comparison of L-type calcium channel blocker with T-type calcium channel blocker. Panel (A): the relative mRNA levels analyzed using quantitative real-time reverse transcription-polymerase chain reaction (qRT-PCR). Panel (B): Nucleocounter (NC-3000) based quantification of cellular uptake by T-type calcium channel blocker compared with L-type calcium channel blocker. All data in the graph represent the mean±SD of 3 independent experiments.

Example 5. Verification of the Effect of L-Type Calcium Channel Blocker on Cp-asiRNAs The effect of another type of calcium channel blocker such as T-type calcium channel blocker was tested. cp-asiGFP (50 nM, 100 nM, 250 nM) and cp-asisurvivin (0.3 µM, 0.5 µM, 1 µM) with Penfluridol and Ethosuximide by concentration were added to HeLa/GFP and HeLa cells. After 48 hours, the relative mRNA levels were analyzed using quantitative real-time reverse transcription-polymerase chain reaction (qRT-PCR). The GFP and Survivin mRNA levels were measured by dividing the Tubulin levels (internal control) (panel A in FIG. 5). Unlike L-type calcium channel blocker, T-type calcium channel blocker did not improve gene silencing efficacy of cp-asiRNAs. Additionally, the cellular uptake was analyzed using Nucleocounter (NC3000) based technique. Cy3 labeled cp-asiGFP with non-DHP L-type and T-type calcium channel blocker were treated into HeLa cells. HeLa cells were incubated with Cy3 labeled cp-asiGFP (100 nM) with non-DHP L-type calcium channel blocker and T-type calcium channel blocker. After 8 hours of incubation, the intracellular fluorescent intensity on a gated cell population was quantified. The intracellular Cy3 signals was measured by NC-3000 and normalized relative to Cy3 labeled cp-asiGFP expression. As seen panel B of FIG. 5, the enhanced cellular uptake of the cp-asiGFP is only detected when treated with non-DHP L-type calcium channel blocker, not T-type calcium channel blocker.

Figure 6:
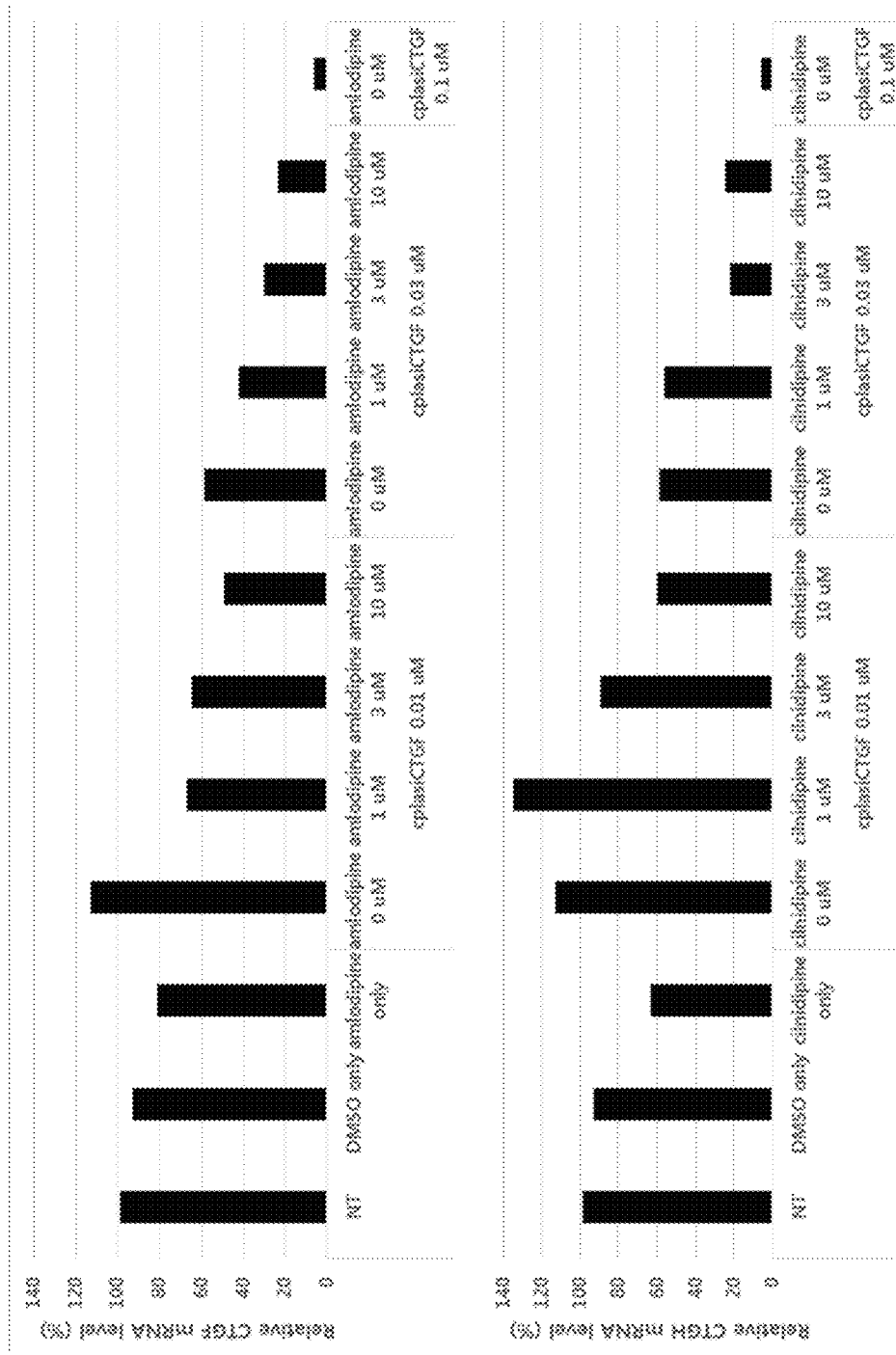
FIG. 6 shows gene silencing efficacy of cplasiRNAs by L-type calcium channel blocker. cp-lasiCTGF (0.01 uM, 0.03 uM, 0.1 uM) with Amlodipine and Cilnidipine by concentration were treated into HeLa cells. After 24 hours, the relative mRNA levels were analyzed using quantitative real-time reverse transcription-polymerase chain reaction (qRT-PCR). The CTGF mRNA levels were measured by dividing the GAPDH levels (internal control).

Example 6. Effect of L-Type Calcium Channel Blocker on Various Form of Cp-asiRNA To identify the effect of L-type calcium channel blocker on various form of cp-asiRNA, structural change and several chemical modification was applied to cp-asiRNA. The resulting RNA molecule, termed cell penetrating long asymmetric siRNA (cp-lasiRNA) showed efficient target gene silencing. cp-lasiRNA targeting CTGF (cp-lasiCTGF) with Amlodipine and Cilnidipine was treated into HeLa cells. Their gene silencing activity was measured by qRT-PCR (FIG. 6). L-type calcium channel blockers such as Amlodipine and Cilnidipine help to enhance the gene silencing effect of cp-lasiRNA in a dose-dependent manner. These results support that L-type calcium channel blocker works on various form of cp-asiRNA to improve the target gene silencing efficacy.

cp-lasiRNA sequence information (SEQ ID NOs: 145 and 146, "m": OMe modification, "*": phosphorothioate (PS) modification, and "chol": cholesterol modification).

```
cp-lasiCTGF   sense      5'-mCUmUAmCCmGAmCUmGGmAA*mG*A*
              strand     chol-3' anti-      5'-UCUUCCAGUCGGUAmAmGmCmCmGmCm
              sense      GmAmGmGmGmCmAm*mG*mG*mC*mC-3
              strand
```

CTGF and GAPDH primer sequence information (SEQ ID NOs: 147-150)

```
CTGF    Forwaid primer   5'-CAAGGGCCTCTTCTGTGACT-3'
        Reverse primer   5'-CCGTCGGTACATACTCCACA-3'

GAPDH   Forward primer   5'-GAGTCAACGGATTTGGTCGT-3'
        Reverse primer   5'-GACAAGCTTCCCGTTCTCAG-3'
```

What is claimed is:

1. A method of gene silencing in a subject, comprising administering to the subject an effective amount of a cell penetrating asymmetric small interfering RNA (cp-asiRNA) or a long-antisense asiRNA (lasiRNA); and an L-type calcium channel blocker comprising cilnidipine, nicardipine, nifedipine, or amlodipine.

2. The method of claim 1, wherein the cp-asiRNA or lasiRNA and the L-type calcium channel blocker are administered as a single pharmaceutical composition.

3. The method of claim 1, wherein the cp-asiRNA or lasiRNA, and the L-type calcium channel blocker are administered as separate pharmaceutical compositions.

4. The method of claim 1, wherein the cp-asiRNA or lasiRNA, and the L-type calcium channel blocker are co-administered.

5. The method of claim 1, wherein the cp-asiRNA or lasiRNA is administered systemically.

6. The method of claim 1, wherein the cp-asiRNA or lasiRNA is administered locally.

7. The method of claim 6, wherein the local administration is to the subject's skin, eyes, or lungs.

8. The method of claim 1, wherein the L-type calcium channel blocker is administered systemically.

9. The method of claim 1, wherein the L-type calcium channel blocker is administered locally.

10. The method of claim 9, wherein the local administration is to the subject's skin, eyes, or lungs.

11. The method of claim 1, wherein one or both of the cp-asiRNA or lasiRNA, and the L-type calcium channel blocker are formulated for topical, pulmonary, or parenteral delivery.

12. The method of claim 1, wherein the cp-asiRNA or lasiRNA targets connective tissue growth factor (CTGF) gene.

13. The method of claim 12, wherein the subject has a CTGF-associated disease or disorder comprising keloid, kidney fibrosis, pachydermatosis, pulmonary fibrosis, hepatic fibrosis, arthritis, renal failure, vasculogenesis-related disorder, or dermatofibrosis.

14. The method of claim 1, wherein the cp-asiRNA or lasiRNA targets MYD88 gene.

15. The method of claim 14, wherein the subject has an ocular disease or disorder comprising an as age-related macular degeneration (AMD).

16. The method of claim 15, wherein the AMD comprises dry or wet AMD.

17. The method of claim 1, wherein the cp-asiRNA or lasiRNA targets a tyrosinase gene.

18. The method of claim 17, wherein the cp-asiRNA or lasiRNA is suitable for treating skin diseases or conditions comprising skin whitening, darkening, or scarring, atopic dermatitis, psoriasis, scleroderma, hair loss, or wrinkled skin.

* * * * *